(12) United States Patent
Telfort et al.

(10) Patent No.: US 9,107,625 B2
(45) Date of Patent: Aug. 18, 2015

(54) PULSE OXIMETRY SYSTEM WITH ELECTRICAL DECOUPLING CIRCUITRY

(75) Inventors: Valery G. Telfort, Montreal (CA); Ammar Al-Ali, Tustin, CA (US); Paul Martek, Pierrefonds (CA)

(73) Assignee: Masimo Corporation, Irvine, CA (US)

( * ) Notice: Subject to any disclaimer, the term of this patent is extended or adjusted under 35 U.S.C. 154(b) by 1024 days.

(21) Appl. No.: 12/436,015

(22) Filed: May 5, 2009

(65) Prior Publication Data

US 2009/0299157 A1    Dec. 3, 2009

Related U.S. Application Data

(60) Provisional application No. 61/050,476, filed on May 5, 2008.

(51) Int. Cl.
*A61B 5/00* (2006.01)
*A61B 5/1455* (2006.01)
(Continued)

(52) U.S. Cl.
CPC ......... *A61B 5/14552* (2013.01); *A61B 5/14551* (2013.01); *G02B 6/42* (2013.01); *G02B 6/43* (2013.01); *H04B 10/802* (2013.01);
(Continued)

(58) Field of Classification Search
CPC ...... H01R 24/20–24/30; H01R 24/38–24/568; H01R 24/58; A61B 2562/22–2562/223; A61B 2562/225–2562/228; A61B 5/1455; G02B 6/42; G02B 6/43; H04B 10/802
USPC ......... 439/92–108; 356/39–42; 307/326–328, 307/89–91
See application file for complete search history.

(56) References Cited

U.S. PATENT DOCUMENTS

| 3,682,161 A | 8/1972 | Alibert |
| 3,808,502 A * | 4/1974 | Babilius ............................ 361/1 |

(Continued)

FOREIGN PATENT DOCUMENTS

| CA | 2262236 | 8/1999 |
| EP | 0716628 | 12/1998 |

(Continued)

OTHER PUBLICATIONS

U.S. Appl. No. 12/904,775, filed Oct. 14, 2010, Fechter et al.
(Continued)

*Primary Examiner* — William Thomson
*Assistant Examiner* — Marie Archer
(74) *Attorney, Agent, or Firm* — Knobbe Martens Olson & Bear, LLP

(57) ABSTRACT

A pulse oximetry system for reducing the risk of electric shock to a medical patient can include physiological sensors, at least one of which has a light emitter that can impinge light on body tissue of a living patient and a detector responsive to the light after attenuation by the body tissue. The detector can generate a signal indicative of a physiological characteristic of the living patient. The pulse oximetry system may also include a splitter cable that can connect the physiological sensors to a physiological monitor. The splitter cable may have a plurality of cable sections each including one or more electrical conductors that can interface with one of the physiological sensors. One or more decoupling circuits may be disposed in the splitter cable, which can be in communication with selected ones of the electrical conductors. The one or more decoupling circuits can electrically decouple the physiological sensors.

19 Claims, 17 Drawing Sheets

(51) Int. Cl.
*H04B 10/80* (2013.01)
*G02B 6/43* (2006.01)
*G02B 6/42* (2006.01)
*H01R 24/00* (2011.01)
*G02B 6/00* (2006.01)
*H04B 10/00* (2013.01)
*H01R 24/22* (2011.01)

(52) U.S. Cl.
CPC ........ *A61B2560/045* (2013.01); *A61B 2562/08* (2013.01); *A61B 2562/222* (2013.01); *A61B 2562/227* (2013.01); *H01R 24/22* (2013.01)

(56) References Cited

U.S. PATENT DOCUMENTS

| | | |
|---|---|---|
| 4,127,749 A | 11/1978 | Atoji et al. |
| 4,326,143 A | 4/1982 | Guth et al. |
| 4,537,200 A | 8/1985 | Widrow |
| 4,884,809 A | 12/1989 | Rowan |
| 4,960,128 A | 10/1990 | Gordon et al. |
| 4,964,408 A | 10/1990 | Hink et al. |
| 5,033,032 A | 7/1991 | Houghtaling |
| 5,041,187 A | 8/1991 | Hink et al. |
| 5,069,213 A | 12/1991 | Polczynski |
| 5,086,776 A | 2/1992 | Fowler, Jr. et al. |
| 5,163,438 A | 11/1992 | Gordon et al. |
| 5,278,627 A | 1/1994 | Aoyagi et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,786,892 A | 7/1998 | Hoek |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,023,541 A * | 2/2000 | Merchant et al. ............... 385/20 |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,188,470 B1 | 2/2001 | Grace |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,486,588 B2 | 11/2002 | Doron et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,520,918 B1 * | 2/2003 | Stergiopoulos et al. ...... 600/490 |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |

(56) References Cited

U.S. PATENT DOCUMENTS

| | | |
|---|---|---|
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,918,878 B2 * | 7/2005 | Brodnick ............... 600/483 |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |

(56) References Cited

U.S. PATENT DOCUMENTS

| | | |
|---|---|---|
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |

(56) References Cited

U.S. PATENT DOCUMENTS

| | | |
|---|---|---|
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 2002/0193670 A1 | 12/2002 | Garfield et al. |
| 2003/0015368 A1 | 1/2003 | Cybulski et al. |
| 2003/0135129 A1* | 7/2003 | Cusimano et al. ............ 600/546 |
| 2004/0158162 A1 | 8/2004 | Narimatsu |
| 2004/0267103 A1* | 12/2004 | Li et al. ......................... 600/323 |
| 2005/0283059 A1 | 12/2005 | Iyer et al. |
| 2006/0047215 A1 | 3/2006 | Newman et al. |
| 2006/0238333 A1 | 10/2006 | Welch et al. |
| 2007/0149864 A1 | 6/2007 | Laakkonen |
| 2007/0185393 A1 | 8/2007 | Zhou et al. |
| 2007/0185397 A1 | 8/2007 | Govari et al. |
| 2007/0282212 A1 | 12/2007 | Sierra et al. |
| 2008/0076972 A1 | 3/2008 | Dorogusker et al. |
| 2009/0018429 A1 | 1/2009 | Saliga et al. |
| 2009/0028173 A1* | 1/2009 | Bliss et al. .................... 370/432 |
| 2009/0093687 A1 | 4/2009 | Telfort et al. |
| 2009/0187065 A1 | 7/2009 | Basinger |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2010/0274099 A1 | 10/2010 | Telfort et al. |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |

(56) References Cited

U.S. PATENT DOCUMENTS

| | | |
|---|---|---|
| 2014/0336481 A1 | 11/2014 | Shakespeare et al. |
| 2014/0343436 A1 | 11/2014 | Kiani |
| 2015/0018650 A1 | 1/2015 | Al-Ali et al. |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 94/05207 | 3/1994 |
| WO | WO 94/13207 | 6/1994 |
| WO | WO 95/29632 | 11/1995 |
| WO | WO 99/53277 | 10/1999 |
| WO | WO 00/10462 | 3/2000 |
| WO | WO 01/34033 | 5/2001 |
| WO | WO 01/78059 | 10/2001 |
| WO | WO 01/97691 | 12/2001 |
| WO | WO 02/03042 | 1/2002 |
| WO | WO 02/24067 | 3/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |

OTHER PUBLICATIONS

U.S. Appl. No. 12/904,789, filed Oct. 14, 2010, Telfort, Valery et al.
U.S. Appl. No. 12/904,823, filed Oct. 14, 2010, Al-Ali et al.
U.S. Appl. No. 12/904,836, filed Oct. 14, 2010, Al-Ali, Ammar.
U.S. Appl. No. 12/904,890, filed Oct. 14, 2010, Telfort et al.
U.S. Appl. No. 12/904,907, filed Oct. 14, 2010, Telfort.
U.S. Appl. No. 12/904,931, filed Oct. 14, 2010, Telfort et al.
U.S. Appl. No. 12/904,938, filed Oct. 14, 2010, Telfort et al.
U.S. Appl. No. 12/905,036, filed Oct. 14, 2010, Kiani et al.
U.S. Appl. No. 12/905,384, filed Oct. 15, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
U.S. Appl. No. 12/905,530, filed Oct. 15, 2010, Al-Ali et al.
U.S. Appl. No. 12/960,325, filed Dec. 3, 2010, Al-Ali, Ammar et al.
Analog Devices, 12-Bit Serial Input Multiplying D/A Converter, Product Data Sheet, 2000.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report, PCT Application PCT/CA2003/000536, Dec. 11, 2003; 2 pages.
International Search Report, PCT Application PCT/US2009/069287, Mar. 30, 2010; 7 pages.
Welch Allyn, ECG ASIC, Product Data Sheete, 2001.
Sierra et al., Monitoring Respiratory Rate Based on Tracheal Sounds. First Expierieances, Proceedings of the 26th Annual Int'l Conf. of the IEEE EMBS (Sep. 2004), 317-320.
WelchAllyn OEM Technologies, ECG ASIC, ECG 3-lead, 5-lead, 12-lead and RESP Signal Processing, ECG ASIC Part No. 000.91163.
International Search Report and Written Opinion from PCT/US2009/042902, mailed Aug. 12, 2009.
Analog Devices, 12-Bit Serial Input Multiplying D/A Converter, DAC8043A. Analog Devices, Inc., 2000.
Avago Technologies, HCNR200 and HCNR201, High-Linearity Analog Optocouplers, Data Sheet, Avago Technologies, Nov. 18, 2008.
US 8,845,543, 09/2014, Diab et al. (withdrawn)

* cited by examiner

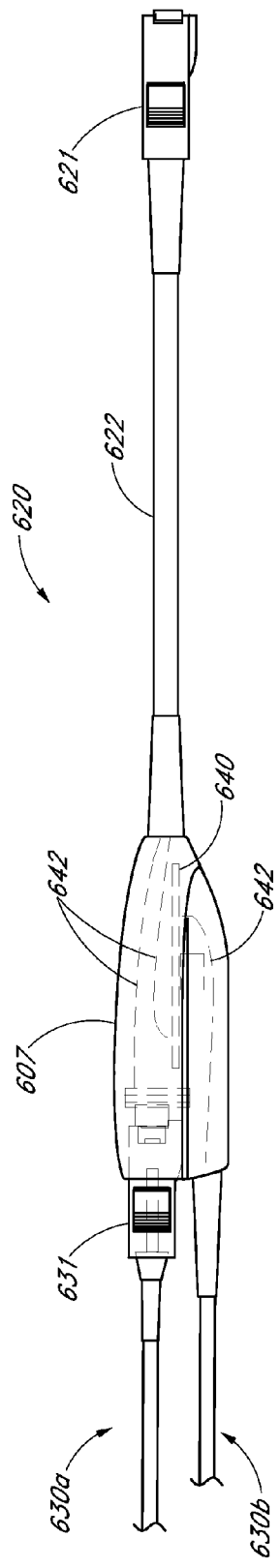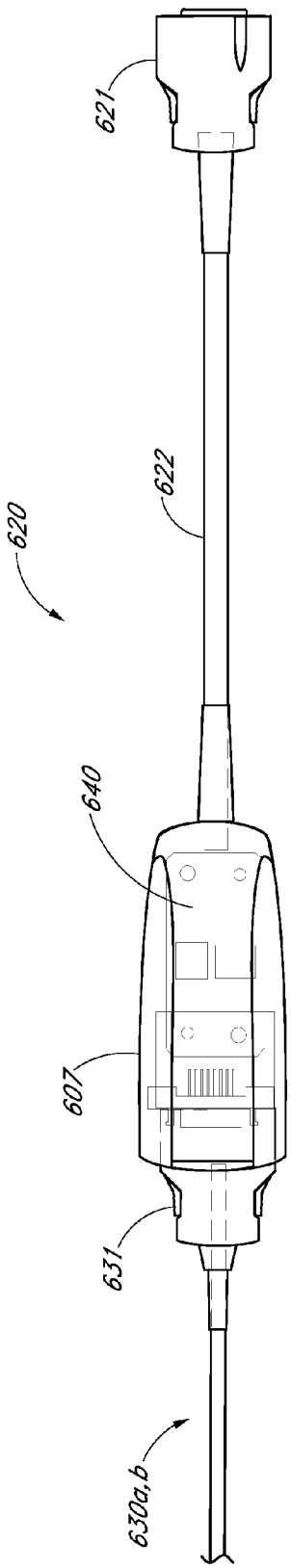
FIG. 6A
FIG. 6B

PULSE OXIMETRY SYSTEM WITH ELECTRICAL DECOUPLING CIRCUITRY

CROSS-REFERENCE TO RELATED APPLICATIONS

The present application claims priority from U.S. Provisional Application No. 61/050,476, titled "Medical Cable Assembly for Reducing the Risk of Electric Shock to a Patient," filed May 5, 2008, which is hereby incorporated by reference in its entirety.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, oxygen saturation ($SpO_2$) level, pulse, and blood pressure, among others. Clinicians, including doctors, nurses, and certain other medical personnel, use the physiological parameters obtained from the medical patient to diagnose illnesses and to prescribe treatments. Clinicians also use the physiological parameters to monitor a patient during various clinical situations to determine whether to increase the level of medical care given to the patient.

Many monitoring devices receive physiological signals from one or more sensors, such as pulse oximetry sensors, acoustic sensors, and the like. Medical cables attached to the sensors transmit signals from the sensors to the monitoring device.

SUMMARY

Certain implementations of a pulse oximetry system for reducing the risk of electric shock to a medical patient include a plurality of physiological sensors, where at least one of the physiological sensors has a light emitter that can impinge light on body tissue of a living patient and a detector responsive to the light after attenuation by the body tissue. The body tissue can include pulsating blood. The detector can generate a signal indicative of a physiological characteristic of the living patient. The medical apparatus may also include a splitter cable having a monitor connector that can connect to a physiological monitor, a plurality of sensor connectors that can each connect to one of the physiological sensors, and a plurality of cable sections each disposed between a sensor connector and the monitor connector, where each of the cable sections have one or more electrical conductors. The one or more electrical conductors for at least some of the cable sections may include a power line that can supply power to one or more of the plurality of physiological sensors, a signal line that can transmit the physiological signals from one or more of the physiological sensors to the physiological monitor, and a ground line that can provide an electrical return path for the power line. Further, the splitter cable may also have one or more decoupling circuits in communication with selected ones of the one or more electrical conductors. The one or more decoupling circuits may communicate physiological signals between one or more of the physiological sensors and the physiological monitor. The one or more decoupling circuits can electrically decouple the physiological sensors, such that the one or more decoupling circuits are configured to substantially prevent ground loops from forming in the ground line.

In certain embodiments, a medical apparatus for reducing the risk of electric shock to a medical patient when used with a pulse oximeter includes a plurality of physiological sensors. At least one of the physiological sensors can include a light emitter that can impinge light on body tissue of a living patient, where the body tissue has pulsating blood. The physiological sensor can also include a detector responsive to the light after attenuation by the body tissue, such that the detector can generate a signal indicative of a physiological characteristic of the living patient. The medical apparatus may also include a splitter cable that can connect the plurality of physiological sensors to a physiological monitor. The splitter cable may include a plurality of cable sections that each includes one or more electrical conductors that can interface with one of the physiological sensors. One or more decoupling circuits can be disposed in the splitter cable. The one or more decoupling circuits can be in communication with selected ones of the one or more electrical conductors. The one or more decoupling circuits can communicate physiological signals between one or more of the physiological sensors and the physiological monitor. The one or more decoupling circuits can electrically decouple the physiological sensors.

Various embodiments of a method for reducing the risk of electric shock to a medical patient as used with a pulse oximeter may include providing a plurality of physiological sensors, where at least one of the physiological sensors has a light emitter that can impinge light on body tissue of a medical patient and a detector that can generate a signal indicative of a physiological characteristic of the living patient responsive to the light after attenuation by the body tissue. The method can also include providing a medical cable assembly having one or more electrical conductors that can allow communication between the plurality of physiological sensors and a physiological monitor, such that the medical cable assembly can provide signals representing physiological information of a medical patient from the plurality of physiological sensors to the physiological monitor. Moreover, the method may include electrically decoupling the plurality of physiological sensors using one or more decoupling circuits disposed in the medical cable assembly. The one or more decoupling circuits may be in communication with the plurality of physiological sensors and with the physiological monitor.

For purposes of summarizing the disclosure, certain aspects, advantages and novel features of the inventions have been described herein. It is to be understood that not necessarily all such advantages may be achieved in accordance with any particular embodiment of the inventions disclosed herein. Thus, the inventions disclosed herein may be embodied or carried out in a manner that achieves or optimizes one advantage or group of advantages as taught herein without necessarily achieving other advantages as may be taught or suggested herein.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 6A illustrates a side view of an example splitter cable;

FIG. 6B illustrates a bottom view of the example splitter cable of FIG. 6A;

DETAILED DESCRIPTION

Multiple sensors are often applied to a medical patient to provide physiological information about the patient to a physiological monitor. Some sensors, including certain optical and acoustic sensors, interface with the monitor using a cable having power, signal, and ground lines or wires. One or more these lines can pose an electric shock hazard when multiple sensors are attached to the patient. If an electrical potential exists in the ground line, for instance, a ground loop can form in the patient or in the ground line, allowing unwanted current to pass through the patient through the ground line. Power fluctuations or surges, such as from a defibrillator, can potentially harm the patient and damage the monitor or the sensors.

This disclosure describes decoupling circuitry that can be used to prevent or substantially prevent ground loops and other current loops from forming. Using decoupling circuitry in this manner can be referred to as providing sensor isolation, patient isolation, patient protection, sensor decoupling, or the like. Currently-available physiological monitors that connect to one sensor at a time using a single cable may not have this decoupling circuitry. Upgrading these monitors to receive two or more sensors can create the shock hazard described above unless protective circuitry is added to these monitors. For existing single-sensor monitors, adding this circuitry might require a costly upgrade of the monitors internal components. For new single-sensor monitors, the decoupling circuitry could be added during manufacturing. But this approach would be cost-inefficient for buyers who wish to use only one sensor with the device.

Accordingly, in certain embodiments, the decoupling circuitry is provided in a medical cable assembly. The medical cable assembly includes, in some embodiments, a splitter cable that interfaces multiple physiological sensors with a single sensor port on a physiological monitor. Advantageously, in certain embodiments, the medical cable assembly allows multiple sensors to connect to a monitor while reducing the risk of electric shock to a patient.

Figure 1:
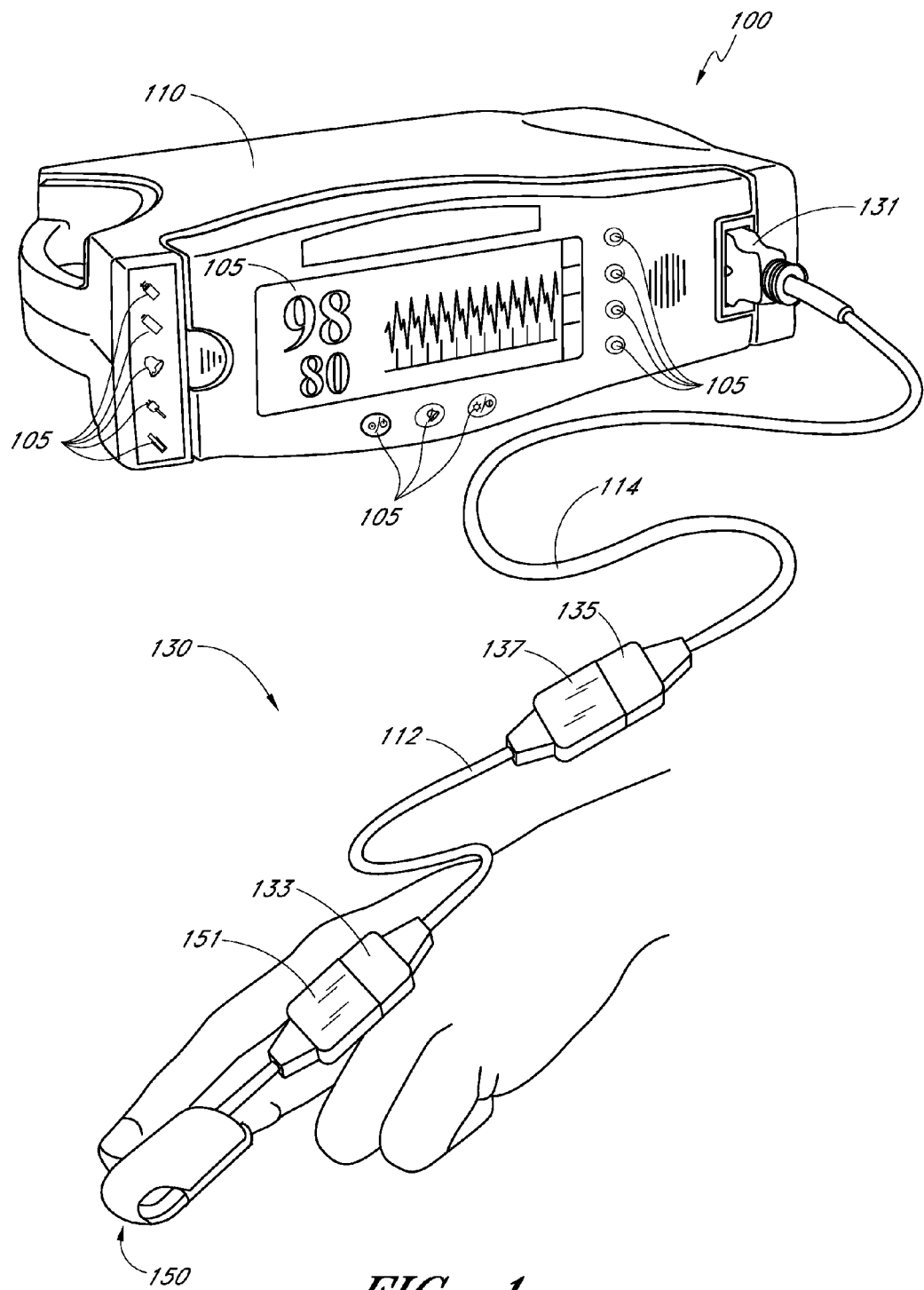
FIG. 1 illustrates a perspective view of an embodiment of a physiological monitoring system.

Turning to FIG. 1, an embodiment of a physiological monitoring system 100 for monitoring a medical patient is shown. The physiological monitoring system 100 includes a physiological monitor 110 coupled with a sensor assembly 150 through a cable 130. The monitor 110 includes various visual indicia and user controls 105 for displaying sensor parameters, alarms, and the like and for receiving user input. The sensor assembly 150 could include any of a variety of physiological sensors. For example, the sensor assembly 150 could include one or more optical sensors that allow the measurement of blood constituents and related parameters, acoustic respiratory sensors, electrocardiograph sensors, and the like.

More generally, the sensor assembly 150 can include one or more sensors that measure one or more of a variety of physiological parameters, including oxygen saturation, carboxyhemologbin (HbCO), methemoglobin (HBMet), fractional oxygen, total hemoglobin (HbT/SpHb), pulse rate, perfusion index electrical heart activity via electrocardiography, and blood pressure. Other examples of physiological parameters that may be measured include respiratory rate, inspiratory time, expiratory time, inspiration-to-expiration ratio, inspiratory flow, expiratory flow, tidal volume, end-tidal $CO_2$ ($ETCO_2$), $CO_2$, minute volume, apnea duration, breath sounds, rales, rhonchi, stridor, changes in breath sounds such as decreased volume or change in airflow, heart rate, heart sounds (e.g., S1, S2, S3, S4, and murmurs), and changes in heart sounds such as normal to murmur or split heart sounds indicating fluid overload.

In some embodiments, the sensor assembly 150 can be an optical sensor having one or more emitters, such as light emitting diodes. The emitters may emit multiple wavelengths of light that impinge on body tissue of a living patient, such as a finger, foot, ear, or the like. The emitters may also emit non-visible radiation. The sensor assembly 150 may further include one or more detectors that can receive light attenuated by the body tissue of the patient. The detectors can generate physiological signals responsive to the detected light. The sensor assembly 150 can provide these physiological signals to the monitor 110 for processing to determine one or more physiological parameters, such as certain of the parameters described above. An example of such a sensor assembly 150 is described in U.S. Publication No. 2006/0211924, filed Mar. 1, 2006, titled "Multiple Wavelength Sensor Emitters," the disclosure of which is hereby incorporated by reference in its entirety.

The cable 130 is connected to the sensor assembly 150 and to the monitor 110. In some embodiments, the cable 130 includes two or more cables or cable assemblies, although it should be noted that the cable 130 can also be a single cable 130. In the illustrated embodiment, the cable 130 includes a sensor cable 112 and an instrument cable 114. The sensor cable 114 is connected directly to the sensor assembly 150 through connectors 133, 151, and the instrument cable 114 is connected directly to the monitor 110 through a connector 131. The sensor cable 112 is connected to the instrument cable 114 through connectors 135, 137.

In certain embodiments, the sensor cable 112 is a lightweight, flexible cable used for a single medical patient and disposed of after use with that patient. In contrast, the instrument cable 112 of certain embodiments is used for multiple patients and may be more durable than the sensor cable 112. For example, the instrument cable 112 may be thicker, stiffer, or heavier than the sensor cable 112. Advantageously, in certain embodiments, the lightweight, flexible characteristics of the sensor cable 112 make the sensor cable 112 more comfortable to attach to a patient. A patient with a sensor assembly 150 attached to her finger, for instance, could more easily move her hand with a lightweight sensor cable 112 attached to the sensor assembly 150. However, if some or all of the cable 130 were lightweight and flexible, it might be less durable. Hence, a portion of the cable 130 (e.g., the instrument cable 114) is stronger and more durable, yet potentially heavier and less flexible. The instrument cable 114 could therefore be used for multiple patients, while the sensor cable 112 might be used for fewer patients, such as a single patient.

Figure 2:
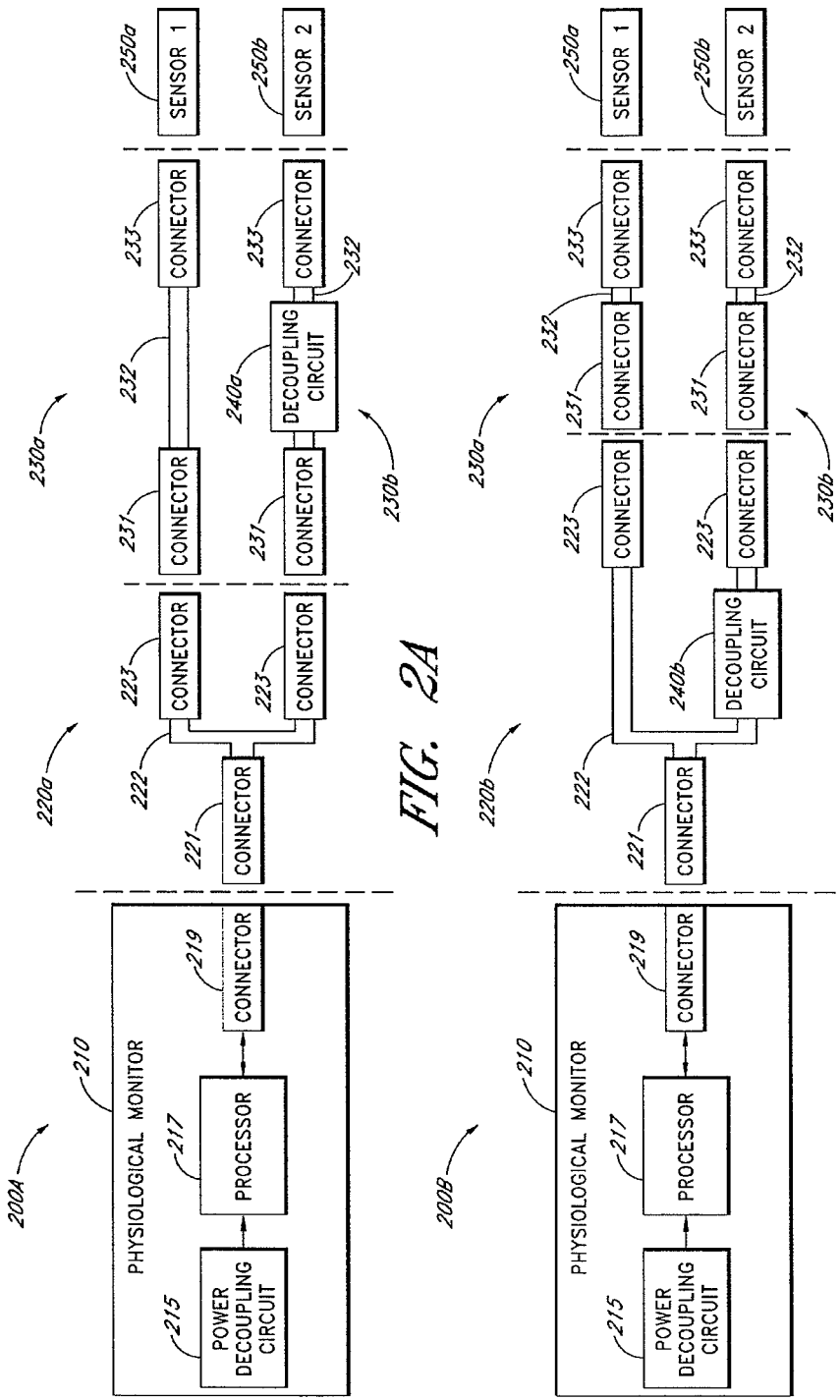
FIGS. 2A and 2B illustrate block diagrams of example physiological monitoring systems having splitter cables.

While the physiological monitor 110 of FIG. 1 is shown connecting to a single sensor assembly 150, it may be advantageous in certain embodiments to connect to multiple sensors, such as sensors that monitor different physiological parameters. For instance, the physiological monitor 110 could connect to a pulse oximetry sensor and an acoustic sensor that measures respiratory rate, heart sounds, and related parameters. One way to provide multiple sensor functionality to the physiological monitor 110 is to provide a splitter cable between the monitor and the cable 130 (see FIGS. 2 and 6). A splitter cable reduces or eliminates a need to build a second cable port into the chassis of the physiological monitor 110 to accommodate a second cable 130. Consequently, using a splitter cable can reduce costs. Moreover, using a splitter cable can reduce cross-talk noise between signal lines from the sensors.

However, as described above, upgrading the physiological monitor 110 to receive input from multiple sensors using a splitter cable or the like can create electrical shock hazards to the patient due to the possibility of conductive paths forming through the sensors, cabling, and the patient. For example, if an acoustic sensor is placed on the chest and a defibrillator paddle touches the acoustic sensor, a surge of current could discharge through a conductive path formed in the patient between the acoustic sensor and a second sensor, and through the physiological monitor 110. This current surge could injure the patient and damage the monitor 110.

Consequently, various embodiments of the cable 130 or an attached splitter cable can include one or more decoupling circuits (not shown) for reducing the risk of electric shock to the patient. Each decoupling circuit can electrically decouple the sensor assembly 150 from the monitor 110 or can decouple multiple sensor assemblies 150. In addition to having its ordinary meaning, electrical decoupling can mean breaking a conductive path (e.g., by providing a dielectric between two conductors) or increasing the resistance between conductors. Electrical decoupling can be accomplished using transformers and/or optocouplers, as described below. The electrical decoupling of the decoupling circuit can prevent or reduce harmful current surges from harming the patient. Example decoupling circuits are described below with respect to FIGS. 2 through 6.

In addition to including decoupling circuitry in the cable 130 or in an attached splitter cable, it may be desirable to include other circuitry in the cable 130 or splitter cable. For example, the cable 130, a splitter cable, and/or the sensor assembly 150 may include one or more information elements (not shown), which can be memory devices such as EEPROMs or the like. In one embodiment, the information element stores cable management information, patient context information, and/or physiological information. Example information elements are described below with respect to FIGS. 6 through 14.

FIGS. 2A and 2B illustrate embodiments of physiological monitoring systems 200A, 200B interfacing with multiple sensor assemblies 250. The physiological monitoring systems 200A, 200B each include a physiological monitor 210, a splitter cable 220, two cables 230, and two sensor assemblies 250. The physiological monitoring systems 200A, 200B may include all of the features of the physiological monitoring system 100 described above.

In the physiological monitoring system 200A of FIG. 2A, a patient decoupling circuit 240a is provided in one of the cables 230b. In the physiological monitoring system 200B of FIG. 2B, the patient decoupling circuit 240b is provided in the splitter cable 220b. These patient decoupling circuits 240a, 240b can reduce or prevent ground loops from forming in the patient and/or in the physiological monitoring system 200. Although not shown, a decoupling circuit could instead be provided in one or both of the sensor assemblies 250.

The physiological monitor 210 processes and outputs physiological information received from sensors included in the sensor assemblies 250a, 250b. The physiological monitor 210 of certain embodiments includes a power decoupling circuit 215, a processing board 217, and a connector 219. The power decoupling circuit 215 may be a transformer or the like that decouples power (e.g., AC electrical power) received from a power source (such as an electrical outlet) and the circuitry of the physiological monitor 210. The power decoupling circuit 215 prevents or substantially prevents current spikes from damaging the other components of the physiological monitor 210 or the patient. In embodiments where the physiological monitor 210 receives power from another source, such as batteries, the power decoupling circuit 215 may not be included.

The processor 217 of certain embodiments is a microprocessor, digital signal processor, a combination of the same, or the like. The processor 217 receives power from the power decoupling circuit 215. In some implementations the processor 217 processes physiological signals received from the sensors 250 and outputs the processed signals to a display, storage device, or the like. In addition, the processor 217 may communicate with an information element (e.g., a memory device) included in a cable or sensor. Information elements are discussed in greater detail below with respect to FIGS. 6 through 14.

The connector 219 includes a physical interface for connecting a cable assembly to the physiological monitor 210. In the embodiment shown in FIGS. 2A and 2B, a single connector 219 is provided. Additional connectors 219 may also be included in some implementations. One embodiment of a physiological monitor having additional connectors 219 is described below with respect to FIG. 3.

The splitter cable 220 is provided in some embodiments to enable the physiological monitor 210 having one connector 219 to interface with multiple sensors 250. The splitter cable 220 interfaces with the connector 219 through a monitor connector 221 in the splitter cable 220. In the depicted embodiment, where the splitter cable 220 interfaces with two sensors 250, cable sections 222 of the splitter cable 220, which branches into two sections generally forming a "Y" shape or the like. Thus, the splitter cable 220 can be a Y cable or the like. While the splitter cable 220 is shown forming a "Y" shape, other configurations and shapes of the splitter cable 220 may be used. For example, the splitter cable 220 could branch into more than two cable sections 222 to interface with more than two sensors 250.

The cable sections 222 are shown connected to the monitor connector 221 and two cable connectors 223. In some embodiments, the cable sections 222 branch into more than two parts and connect to more than two cable connectors 223. In addition, in some embodiments the splitter cable 220 couples directly to two or more sensors 250.

Some embodiments of the splitter cable 220 include one or more lines, conductors, or wires per cable connector 223. One line might be provided, for example, to interface with one or more electrocardiograph (ECG) sensors. Two or three lines might be provided per cable connector 223, for example, to interface with an optical or acoustic sensor. For instance, three lines might be provided, including a power line, a signal line, and a ground line (see FIGS. 4 and 5). The power line powers the sensor 250, the signal line receives signals from the sensor 250, and the ground line acts as an electrical return path for the power and/or signal lines. In some embodiments, one or more of the lines coming from one sensor 250a are placed at a predetermined distance from one or more of the lines coming from another sensor 250b to reduce cross-talk interference between the sensors 250. One or more electromagnetic shielding and/or insulating layers may also be provided to help reduce cross-talk. Lines from different sensors may merge into a shared line that connects electrically to the monitor 210, and some form of multiplexing might be used to allow the different sensors to communicate along the shared lines.

The cables 230a, 230b interface with the splitter cable 220 in the depicted embodiment through cable connectors 231. In certain embodiments, each cable 230 also includes a cable section 232 and a sensor connector 233 that connects to a sensor 250. The cable section 232 in some implementations includes one or more lines or wires for communicating with the sensor 250. For example, a power line, sensor line, and ground line may be provided that correspond to the power line, sensor line, and ground line in the example splitter cable 220 described above.

In an embodiment, one of the cables 230 includes the decoupling circuit 240a. In FIG. 2A, for example, the decoupling circuit 240a is shown in the cable section 232 of the cable 230b. The decoupling circuit 240a may also be placed in the cable connector 231 or the sensor connector 233, or in a combination of one or more of the connectors 231, 233 and/or the cable section 232. In another exemplary embodiment, FIG. 2B shows that the decoupling circuit 240b can be included in one of the cable sections 222 of the splitter cable 220b. The decoupling circuit 240b may also be placed in the monitor connector 221 or the sensor connector 223, or in a combination of the cable sections 222 and/or one or more of the connectors 221, 223.

Multiple decoupling circuits 240 may also be provided in one or more of the cables 230 and/or in the splitter cable 220 in other embodiments. In particular, in one embodiment when N cables 230 are provided (or one splitter cable 220 with N connectors 223), N−1 decoupling circuits 240 are provided in N−1 of the cables 230 or in the various sections of the splitter cable 220.

The decoupling circuit 240 of certain embodiments electrically decouples a sensor 250 from the physiological monitor 210. In addition, the decoupling circuit 240 can electrically decouple one sensor (e.g., the sensor 250b) from another sensor (e.g., the sensor 250a) in certain embodiments. The decoupling circuit 240 can be a transformer, an optocoupler, a DC-DC converter, a switched-mode converter, or the like or a combination of the foregoing. In addition, the decoupling circuit 240 can include one or more optical fibers. An optical fiber may be used in place of the signal line, for example. More detailed embodiments of the decoupling circuit 240 are described below with respect to FIGS. 4 and 5.

The sensors 250 connect to the sensor connectors 233 of the cables 230. In an embodiment, one of the sensors 250 is an optical sensor, such as a multiple wavelength oximetry sensor. The other sensor 250 in one embodiment is an acoustic sensor. In addition, the sensor 250 may be an acoustic sensor that also monitors ECG signals, such as is described in U.S. Provisional Application No. 60/893,853, titled "Multi-parameter Physiological Monitor," and filed Mar. 8, 2007, the disclosure of which is hereby incorporated by reference in its entirety. Many other types of sensors 250 can also be used to monitor one or more physiological parameters.

Figure 3:
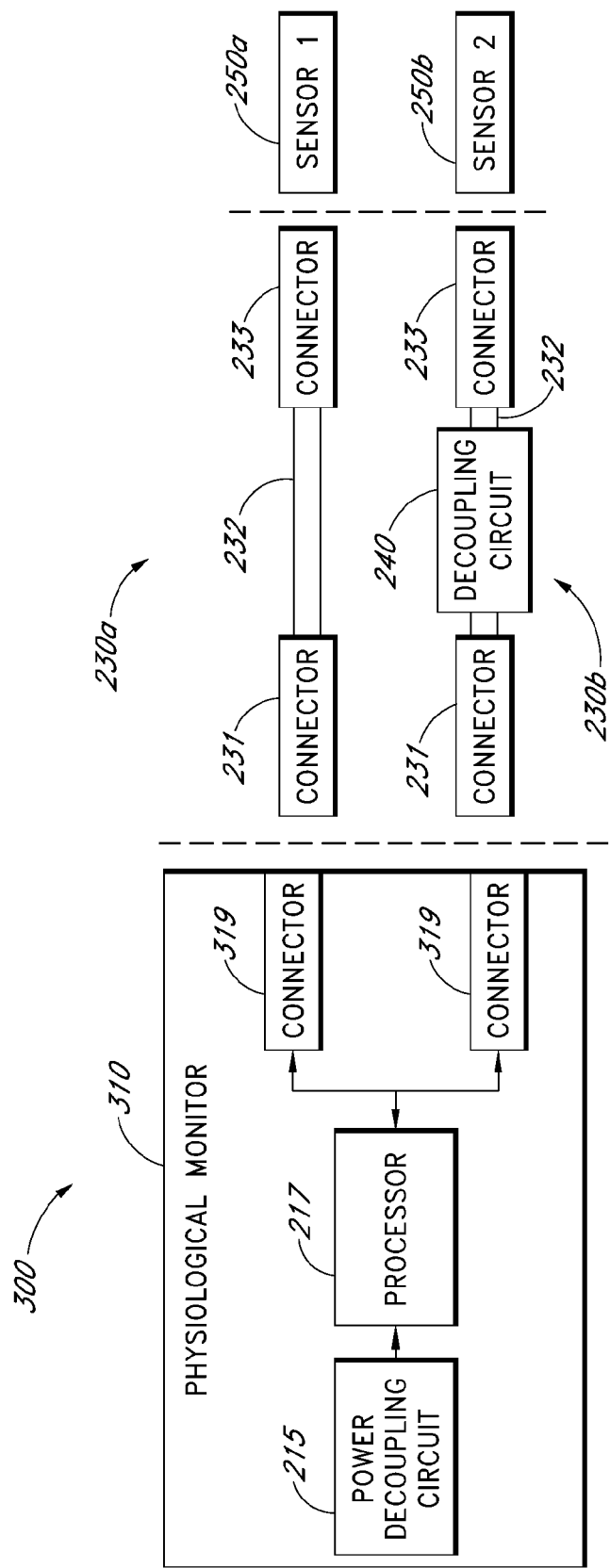
FIG. 3 illustrates a block diagram of another embodiment of a physiological monitoring system having multiple cables.

FIG. 3 illustrates another embodiment of a physiological monitoring system 300 having multiple cables 230. The physiological monitoring system 300 may have certain of the features of the physiological monitoring systems 100, 200 described above. For example, like the physiological monitoring system 200 described above, the physiological monitoring system 300 includes a physiological monitor 310, two cables 230, and two sensors 250. In the physiological monitoring system 300, a decoupling circuit 240 is provided in one of the cables 230b.

Like the physiological monitor 210, the physiological monitor 310 includes a power decoupling circuit 215 and a processor 217. Unlike the physiological monitor 210, however, the physiological monitor 310 includes two connectors 319 for interfacing directly with two cables without using a splitter cable. To save costs for users who will use only one sensor 250 with the physiological monitor 310, a decoupling circuit 240 is not provided in the physiological monitor 310. Instead, the decoupling circuit 240 can be provided in a separate cable 230b that can be used with the physiological monitor 310.

For example, a user might use one cable 230a and sensor 250a at a time with the physiological monitor 310. Since only one sensor 250a is being used, ground or other current loops are less likely to form in the patient. If the user later wishes to use additional sensors 250, the user can obtain a cable 230b having the decoupling circuit 240. Using the cable 230b can beneficially allow the user to continue using the physiological monitor 310 without performing an upgrade to the physiological monitor's 310 internal components.

Figure 4:
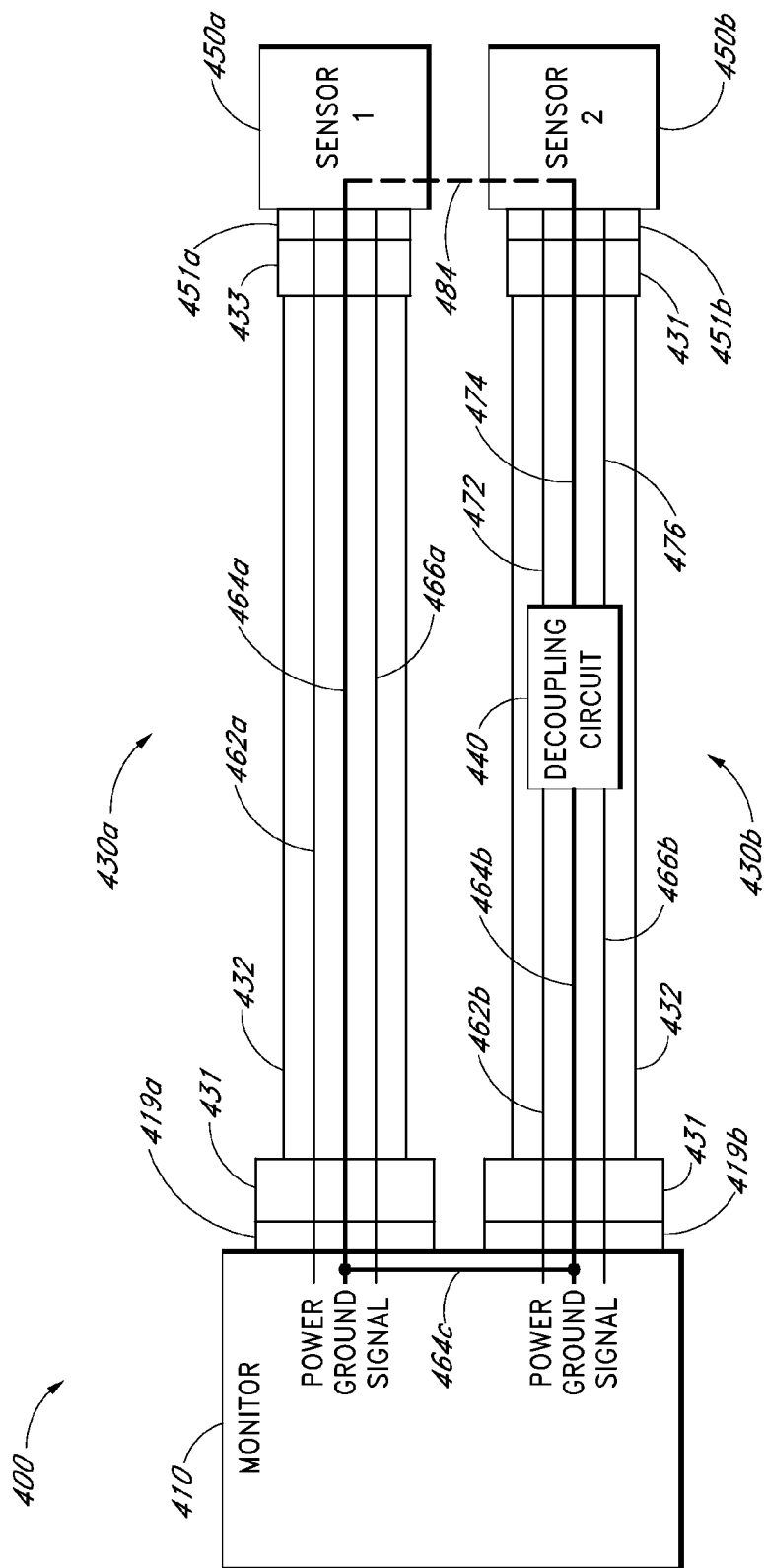
FIG. 4 illustrates a block diagram of yet another embodiment of a physiological monitoring system having multiple cables.

FIG. 4 illustrates another embodiment of a physiological monitoring system 400 having multiple cables 430. The physiological monitoring system 400 may have certain of the features of the physiological monitoring systems 100, 200, 300 described above. For example, like the physiological monitoring systems described above, the physiological monitoring system 400 includes a physiological monitor 410, two cables 430, and two sensors 450. The features described with respect to FIG. 4 may also be applied to a monitoring system having a splitter cable instead of multiple cables.

In the depicted embodiment, the cables 430 are shown connected to the physiological monitor 410 and to the sensors 450. Connectors 419 in the physiological monitor 410 couple with connectors 431 of the cables 430, and connectors 433 of the cables couple with connectors 451 of the sensors 450. A cable section 432 extends between the connectors 431, 433 of each cable.

The cable 430a includes a power line 462a, a ground line 464a, and a signal line 466a extending from the connector 431 to the connector 433. These lines form electrical connections with corresponding power, ground, and signal lines in the connector 419a of the physiological monitor 410 and in the connector 451a of the sensor 450a. Likewise, the cable 430b includes a power line 462b, a ground line 464b, and a signal line 466b. These lines form electrical connections with corresponding power, ground, and signal lines in the connector 419b of the physiological monitor 410. In addition, these lines extend from the connector 431 to a decoupling circuit 440. A power line 472, ground line 474, and signal line 476 extend from the decoupling circuit 440 to the connector 431 to form electrical connections with corresponding power, signal, and ground lines in the connector 451b of the sensor 450b. The cable section 432 can also include one or more electrical insulation and shielding layers, materials, or fillers. Although not shown, one or more of the cables 430a, 430b may also include one or more communications lines for communicating with information elements.

In the depicted embodiment, the ground line 464a is connected to the ground line 464b in the physiological monitor 410 through line 464c. When both sensors 450 are placed on a patient, the ground lines 464a and 474b may also be in electrical communication through the patient, as illustrated by the dashed line 484. If the decoupling circuit 440 were not present in one of the cables 430, a ground loop might be formed along the lines 464a, 464b, 464c, 474, and 484 (illustrated with bold lines) due to, for example, a difference in electrical potential in the lines 464a, 464b, 464c, and 474. While not shown in bold, current loops might also form in some cases among the power lines 462a, 462b, 472 or the signal lines 466a, 466b, 476.

Advantageously, in certain embodiments, the decoupling circuit 440 reduces the risk of a ground or other loop forming by decoupling one or more of the power lines 462b, 472, the signal lines 464b, 474, or the ground lines 464b, 474. More detailed embodiments illustrating how the decoupling circuit 440 could decouple one or more lines is described below with respect to FIGS. 5A through 5C and FIG. 8C.

While only one decoupling circuit is shown, in other embodiments, multiple decoupling circuits may be provided in one cable 430. For instance, a first decoupling circuit could be connected to the power line 462b and the ground line 466b, and a second decoupling circuit could be connected to the signal line 464b and to the ground line 466b. In addition, in certain embodiments, there may be a decoupling circuit in each cable 430a, 430b.

Figure 5A:
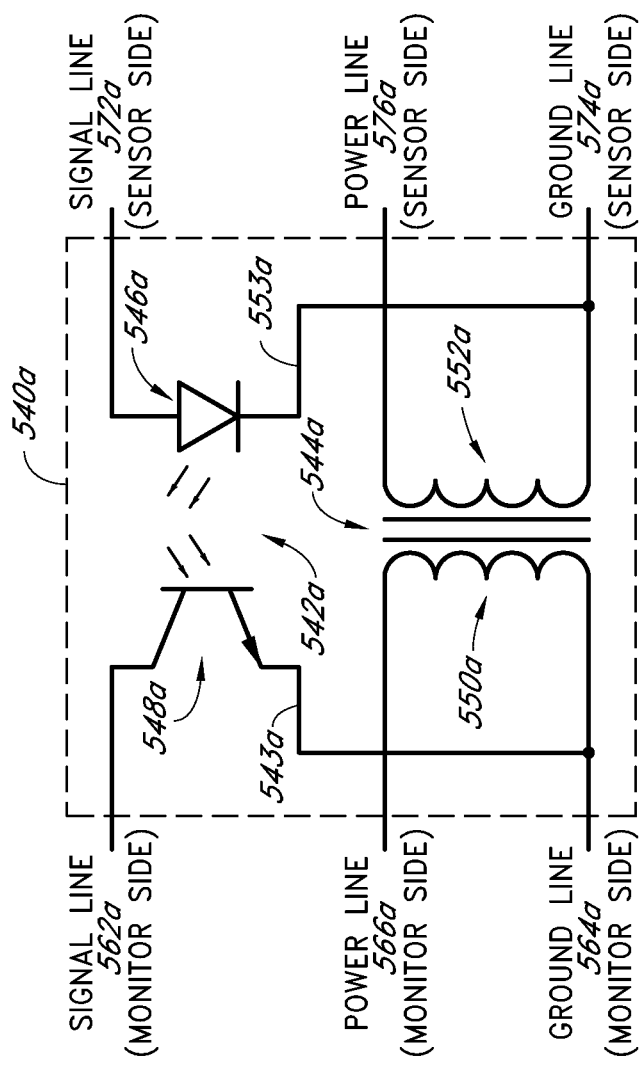
FIGS. 5A through 5C illustrate embodiments of decoupling circuits.

FIG. 5A illustrates a more detailed embodiment of a decoupling circuit 540a suitable for use with any of the embodiments discussed herein. The decoupling circuit 540a may include all the features of the decoupling circuits 240, 340, and 440 described above. For example, the decoupling circuit 540a may be included in a medical cable assembly, such as a splitter cable, medical cable, or the like, or in a sensor assembly. The decoupling circuit 540a can decouple electrical signals and prevent or reduce ground or other conducting loops from forming and can protect against current surges in a multi-sensor physiological monitoring system.

The decoupling circuit 540a is shown within dashed lines. The decoupling circuit 540a of various embodiments receives a signal line 562a, a power line 566a, and a ground line 564a. These lines can be connected to a physiological monitor (not shown). In addition, the decoupling circuit 540a receives a signal line 572a, a power line 576a, and a ground line 574a, which may be connected to a sensor (not shown).

In an embodiment, the power line 566a provides power from a physiological monitor to the decoupling circuit 540a, which provides the power to the sensor through the power line 576a. The signal line 572a provides a physiological signal from the sensor to the decoupling circuit 540a, which provides the physiological signal to the monitor through the signal line 562a. The ground lines 564a and 574a act as return paths for their respective signal and power lines 562a, 566a, 572a, 576a.

The decoupling circuit 540a, in some implementations, includes an optocoupler 542a and a transformer 544a. The optocoupler 542a receives physiological signals from the sensor line 572a and provides the signals to the sensor line 562a optically using, for example, a photodiode 546a and a phototransistor 548a. Because the signals are transmitted optically, in certain embodiments there is no electrical contact between the signal lines 562a, 572a. Similarly, the transformer 544a provides power from the power line 566a to the power line 576a without electrical contact between the lines 566a, 576a. Through mutual inductance, electromagnetic energy is transferred from one winding 550a of the transformer 544a to another winding 552a. Because the signals are transmitted using mutual inductance, there is no electrical contact between the power lines 566a, 576a.

In certain embodiments, because the power lines 566a, 576a and signal lines 562a, 572a are electrically decoupled, the ground lines 564a, 574a can also be electrically decoupled. As shown, a ground line 543a of the optocoupler 542a on the monitor side connects to the ground line 564a, and a ground line 553a of the optocoupler 542a on the sensor side connects to the ground line 574a. As a result, the risk of ground loops forming in the patient may be reduced or eliminated.

Many other configurations of the decoupling circuit 540a may be employed. For instance, a second optocoupler 542a may be used in place of the transformer 544a, or a second transformer 544a may be used in place of the optocoupler 542a. In addition, some forms of DC-DC converters or switched mode converters may be used in place of either the optocoupler 542a or the transformer 544a. Alternatively, one or more optical fibers may be used.

Moreover, one or more optical fibers can be used instead of the optocoupler 542a or the transformer 544a. Because the optical fibers transmit optical, rather than electrical signals, using optical fibers in certain embodiments beneficially reduces the likelihood of ground loops forming in the patient. In one example embodiment, the optocoupler 542a in FIG. 5A is replaced with an optical fiber, but the transformer 544a is still included in the decoupling circuit 540a. The optical fiber allows signals to be transmitted through the signal line while preventing current from passing through the signal line. In addition, if optical fibers are used for the signal lines of multiple sensors, the optical fibers can also reduce cross-talk interference among the signal lines.

Figure 5B:
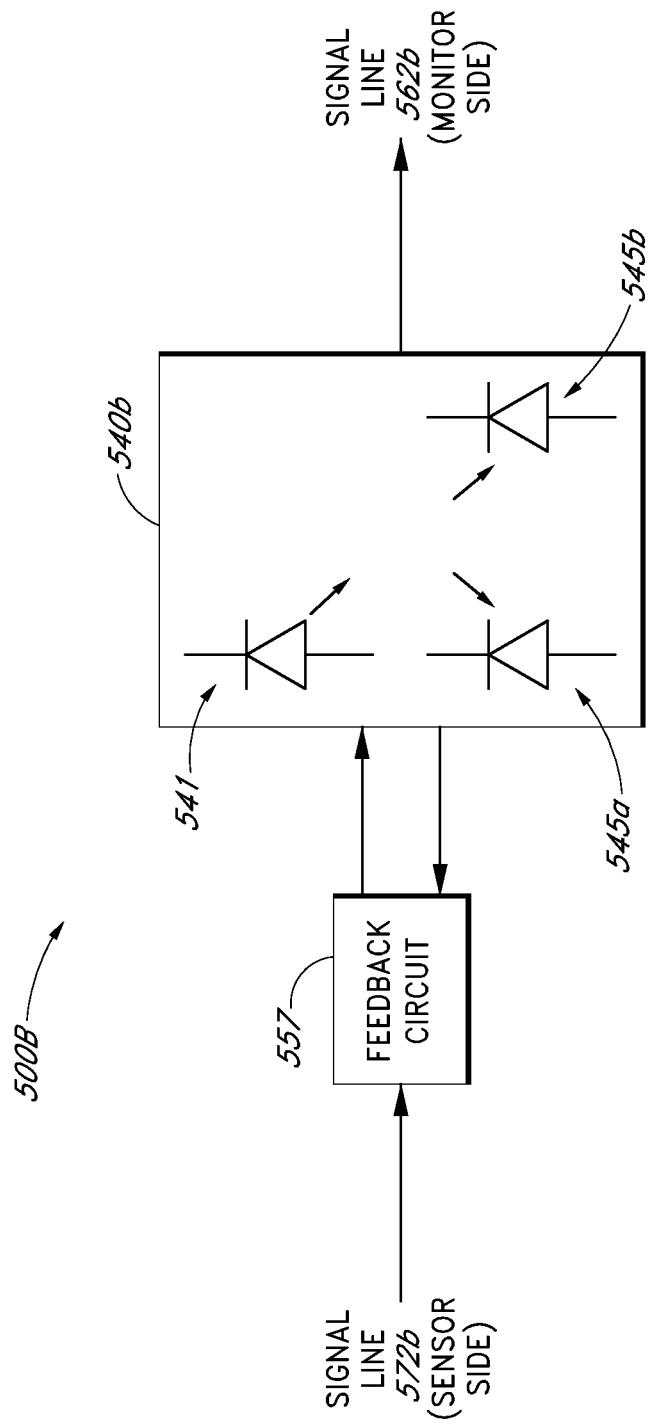

FIG. 5B illustrates an embodiment of a circuit 500B that includes a decoupling circuit 540b. The decoupling circuit 540b may include all the features of the decoupling circuits 240, 340, and 440 described above. For example, the decoupling circuit 540b may be included in a medical cable assembly, such as a splitter cable, medical cable, or the like, or in a sensor assembly.

The decoupling circuit 540b is shown decoupling a signal line 562b connected to a monitor from a signal line 572b connected to a sensor. In the depicted embodiment, the decoupling circuit 540b is an analog optocoupler. The decoupling circuit 540b includes a transmitting photodiode 541 and two receiving photodiodes 545a, 545b for feedback control.

The transmitting photodiode 541 receives physiological signals from the signal line 572b via a feedback circuit 557 (described below). The transmitting photodiode 541 transmits the physiological signals to both of the receiving photodiodes 545a, 545b. The receiving photodiode 545b transmits the signals it receives from the transmitting photodiode 541 to the monitor via signal line 562b. The receiving photodiode 545a transmits the signals it receives to a feedback circuit 557.

Many diodes are inherently unstable due to nonlinearity and drift characteristics of the diodes. As a result of such instability, the signal produced by the transmitting photodiode 541 may not correspond to the signal provided by the signal line 572b from the sensor. The receiving diode 545a can therefore be used as a feedback diode to provide a received signal to the feedback circuit 557.

The feedback circuit 557 can include an amplifier or the like that adjusts its output provided to the transmitting photodiode 541 based at least partly on a difference between the signal of the transmitting photodiode 541 and the receiving diode 545*a*. Thus, the feedback circuit 557 can correct for errors in the transmitted signal via feedback from the feedback or receiving diode 545*a*.

Figure 5C:
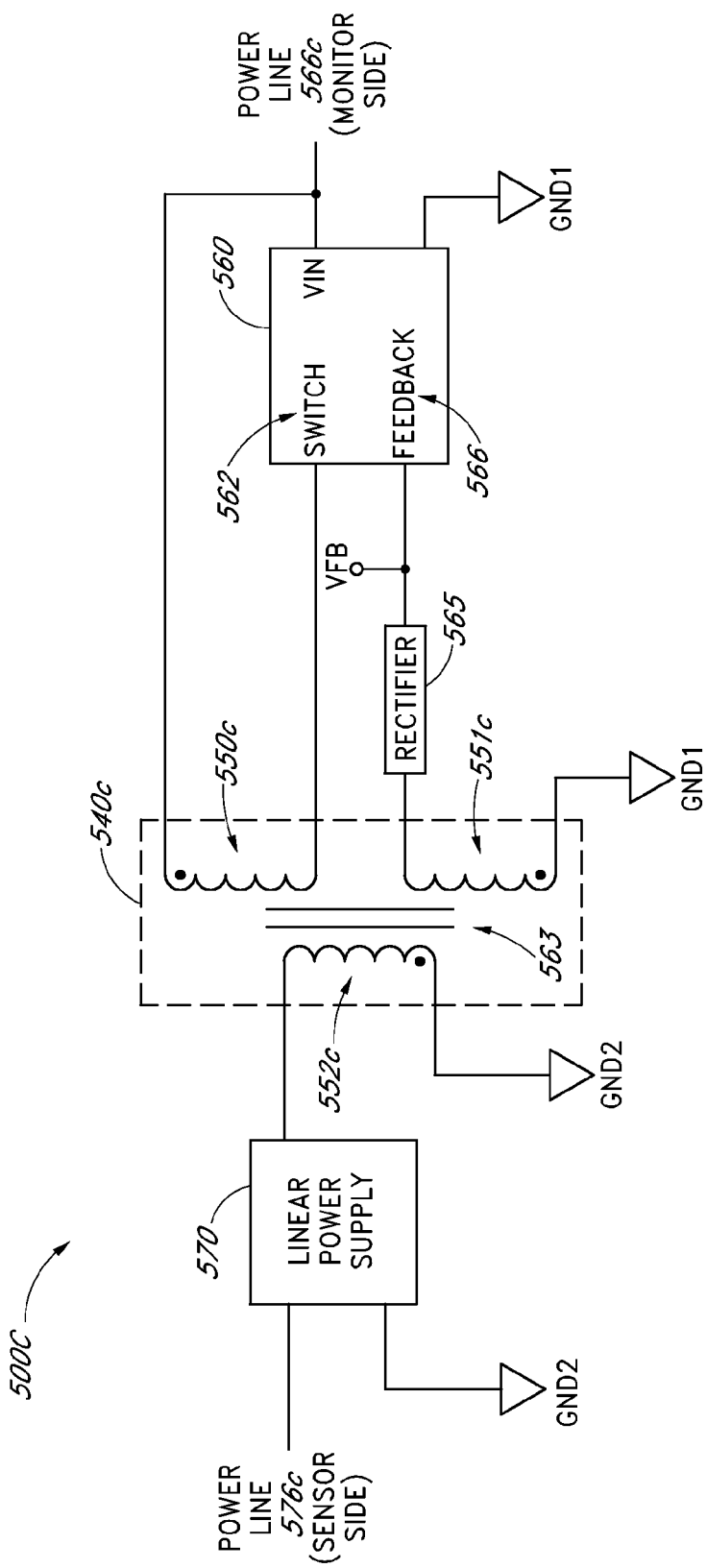

FIG. 5C illustrates another embodiment of a circuit 500C that includes a decoupling circuit 540*c*. The decoupling circuit 540*c* may include all the features of the decoupling circuits 240, 340, and 440 described above. For example, the decoupling circuit 540*c* may be included in a medical cable assembly, such as a splitter cable, medical cable, or the like, or in a sensor assembly.

The decoupling circuit 540*c* is shown decoupling a power line 566*c* connected to a monitor from a power line 576*c* connected to a sensor. The decoupling circuit 540*c* can be used together with the decoupling circuit 540*b* of FIG. 5B in some embodiments. For example, the decoupling circuits 540*b*, 540*c* may be provided on the same circuit board. Like the decoupling circuit 540*b*, the decoupling circuit 540*c* uses feedback to dynamically correct or control the output of the decoupling circuit 540*c*.

The decoupling circuit 540*c* in the depicted embodiment is a flyback transformer having two primary windings 550*c*, 551*c* and one secondary winding 552*c*. The primary winding 550*c* receives power (VIN) from the power line 566*c*. A switched mode power supply 560 also receives power (VIN) from the power line 566*c*. In an embodiment, the switched mode power supply 560 is a DC-DC converter or the like. A switch pin 562 of the power supply 560 can be enabled or otherwise actuated to allow power (VIN) to cycle through the primary winding 550*c*. The switch pin 562 may cause the power to be switched according to a predetermined duty cycle. Feedback may be used, as described below, to maintain a stable or relatively stable duty cycle.

As the primary winding 550*c* is being energized, the primary winding 550*c* may store energy in itself and in a core 563 of the transformer. Through inductive coupling, this energy may be released into the secondary winding 552*c* and into the primary winding 551*c*. The polarity of the windings 552*c*, 551*c* (as indicated by the dots on the windings) may be the same to facilitate the transfer of energy. Likewise, the polarity of the windings 552*c*, 551*c* may differ from the polarity of the winding 550*c*.

Like the feedback receiving photodiode 545*a* described above, the primary winding 551*c* acts as a flyback winding in certain embodiments to transmit the received power as a feedback signal. A rectifier 565 rectifies the power received from the primary winding 551*c* and provides a feedback power VFB to a feedback pin 566 of the power supply 560. The power supply 560 may then use the difference between the received feedback power VFB and the transmitted power VIN to adjust VIN to compensate for any error in the transmitted power. For example, the power supply 560 can adjust the duty cycle described above based at least partly on the error, e.g., by increasing the duty cycle if the VFB is low and vice versa. This flyback operation can advantageously maintain a stable or substantially stable power duty cycle despite varying load conditions on the decoupling circuit 540*c*.

The secondary winding 550*c* can provide an output to a linear power supply 570, which may rectify the received power, among other functions. The linear power supply 570 may provide the power to the power line 576*c* for transmission to the sensor.

FIGS. 6A and 6B illustrate an example splitter cable 620. FIG. 6A depicts a side view of the splitter cable 620 while FIG. 6B depicts a bottom view of the splitter cable 620. The splitter cable 620 includes a housing 607 that includes a circuit board 640 having a decoupling circuit, show in phantom. The housing 607 further includes wires 642, also shown in phantom, in communication with the circuit board 640 and with first cable sections 630*a*, 630*b* and a second cable section 622 of the splitter cable 620. The housing 607 is also shown connected to the second cable section 622, which in turn connects to a connector 621. In an embodiment, the connector 621 is used to connect the splitter cable 620 to a physiological monitor.

The housing 607 of the splitter cable 620 further connects to one of the first cable sections 630*a* through a connector 631. Another one of the first cable sections 630*b* is integrally coupled to the housing 607 of the splitter cable 620 in the depicted embodiment. In one implementation, the splitter cable 620 and the cable 630*b* are used to obtain physiological information from a single sensor, and the cable 630*a* may be added to the splitter cable 620 to obtain physiological information from an additional sensor. It should be noted that in an alternative embodiment, the first cable section 630*b* is not integrally attached to the housing 607 but instead attaches to the housing a second connector. Or, both of the first cable sections 630 could be integral to the housing 607.

The circuit board 640 interfaces with both first cable sections 630*a*, 630*b* and with the second cable section 622. The circuit board 640 may include, for example, one or more integrated circuits or discrete circuit components that together are implemented as a decoupling circuit. In addition, the circuit board 640 can include one or more information elements for storing various forms of data.

Figure 7:
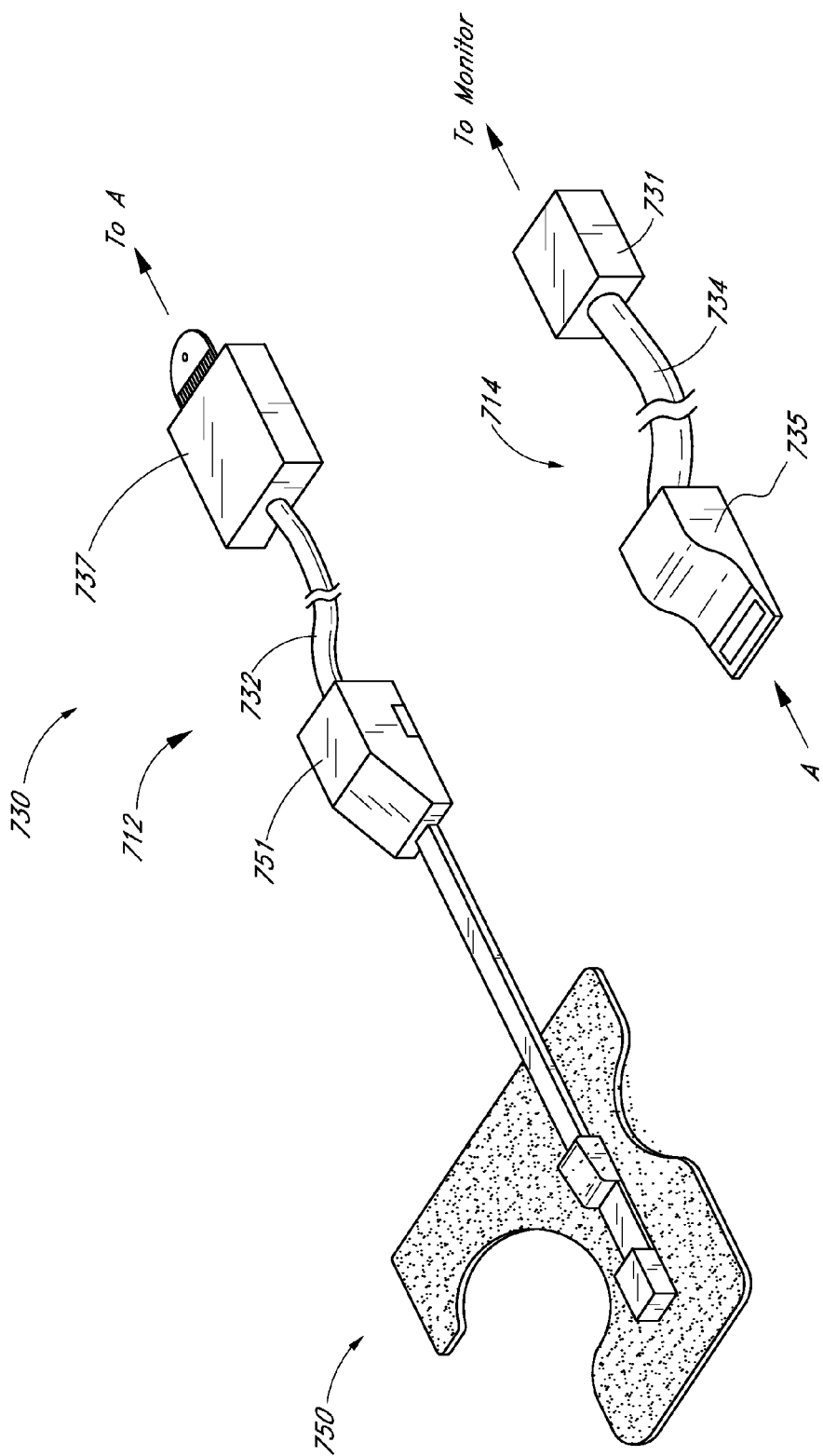
FIG. 7 illustrates a perspective view of an example sensor and cable assembly.

Turning to FIG. 7, additional embodiments of cable assemblies 730 will be described. As explained above with respect to FIG. 1, cable assemblies having two separate cables may be provided in some embodiments. These separate cables can include a sensor cable 712 and an instrument cable 714. In one embodiment, the sensor cable 712 is a short, lightweight cable, adapted to facilitate comfortable attachment of sensors to a medical patient. In certain embodiments, the instrument cable 714 is a heavier, sturdier cable, acting as a durable interface between the sensor cable 712 and a monitor. Sensor cables 712 and instrument cables 714 may be periodically replaced. Periodic replacement is advantageous in certain embodiments for a wide variety of reasons. For example, the cable can become soiled or damaged, causing cable failure inaccurate results, or patient cross-contamination.

In addition, one or more decoupling circuits or information elements (see FIGS. 7 and 8) may be incorporated into the cable assembly 730 in certain embodiments. The information elements may store cable management information related to usage of the cable assembly and devices connected to the cable assembly. The information elements may also store patient context information related to patient identification and patient movement (flow) among hospital departments, thereby tracking the patient's progress throughout the hospital. Examples of patient context information are described more fully in U.S. patent application Ser. No. 11/633,656, titled "Physiological Alarm Notification System," filed Dec. 4, 2006, which is hereby incorporated by reference in its entirety. Moreover, the information elements can store physiological information in some implementations.

Referring again to FIG. 7, a sensor cable 712 is shown connected to a sensor assembly 750. The sensor cable 712 may include a flexible cable section 732 having an elongated shape, a connector 751 for interfacing with a sensor assembly 750, and a connector 737 for interfacing with an instrument cable 714. The flexible nature of the cable section 732 in one embodiment is provided to enable greater patient comfort, as the patient can move more easily with a flexible sensor cable 712 attached.

The depicted example instrument cable 714 includes a stiff or relatively rigid, durable cable section 734 having an elongated shape, a connector 735 for interfacing with the sensor cable 712, and a connector 731 for interfacing with a physiological monitor. As the instrument cable 714 of various embodiments is not connected directly to the patient, the instrument cable section 734 may be less flexible (and more durable) than the sensor cable section 732, thereby extending the life of the instrument cable 714.

Decoupling circuitry and/or information elements may be included within the sensor cable 712, the instrument cable 714, or both. The decoupling circuits and/or information elements may be placed in any of the connectors 737, 751, 735, or 731 or in either cable section 732, 734. In other embodiments, one or more information elements may be included in any of the splitter cables described above. In alternative embodiments, the sensor cable 712 can be a splitter cable.

Figure 8A:
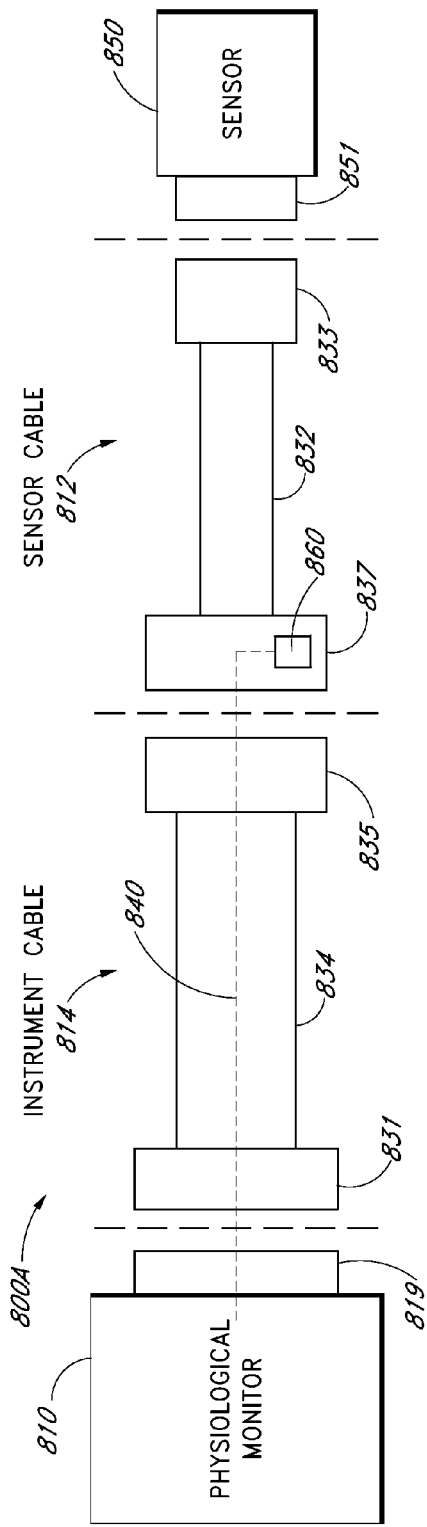
FIGS. 8A and 8B illustrate block diagrams of example cables that include one or more information elements.
Figure 8B:
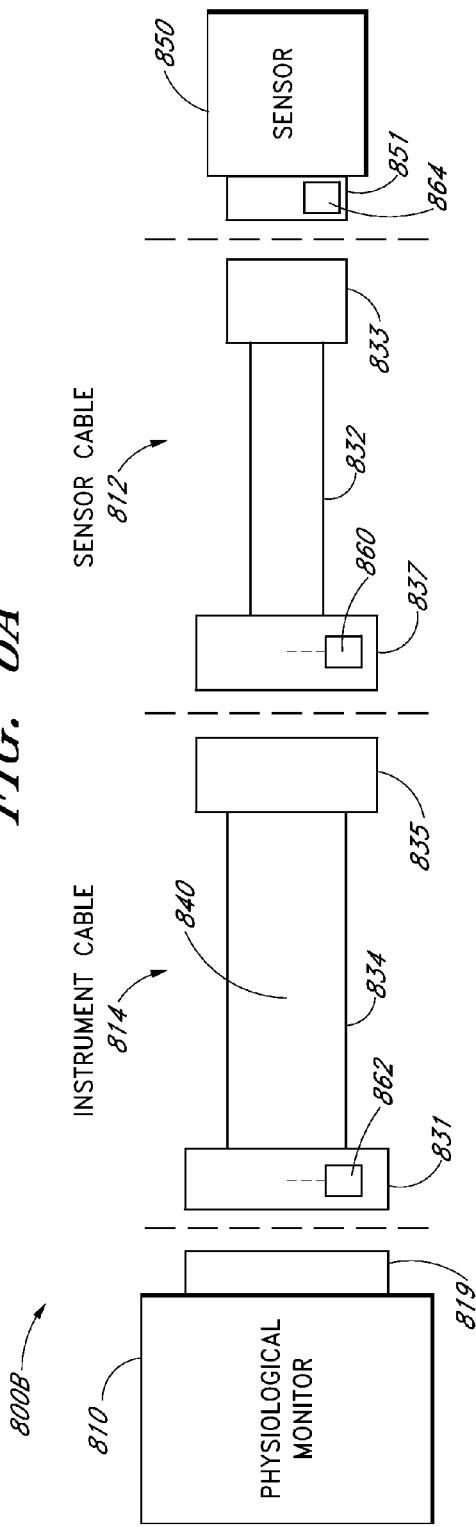

FIGS. 8A and 8B illustrate example layouts of a physiological monitoring system 800. FIGS. 8A and 8B illustrate various information elements 860, 862, and 864. The information elements 860, 862, and 864 may be used to store cable management information, patient context information, and/or physiological information. Although not shown, the information elements 860, 862, and 864 may also be used in the splitter cable embodiments described above. Moreover, decoupling circuitry may be included in the cables of FIGS. 8A and 8B.

Referring to FIG. 8A, a physiological monitoring system 800A includes a physiological monitor 810 that communicates with a sensor 850 through an instrument cable 814 and a sensor cable 812. An information element 860 is included in the sensor cable 812.

The physiological monitor 810 interfaces with the instrument cable 814 using a connector 819, which mates with a connector 831 of the instrument cable 814. The instrument cable 814 mates in turn with the sensor cable 812 through a connector 835 on the instrument cable 814 and a corresponding connector 837 on the sensor cable 812. The sensor cable 812 in turn connects to a sensor 850 through a connector 833 and a corresponding connector 851 on the sensor 850. In alternative embodiments, the sensor cable 812 may be a splitter cable.

In the embodiment shown, the information element 860 is located in the connector 837. Other placements for the information element 860 are also possible. For example, the information element 860 could be located anywhere in the sensor 850 or in the sensor cable 812, including in a sensor cable section 832 or the connector 833. In addition, the information element 860 could also be located in the instrument cable 814 instead, or two or more information elements 860 could be used, one or more in each cable 812, 814 (see, e.g., FIG. 8).

The information element 860 can include any one or more of a wide variety of information elements. In an embodiment, the information element 860 is a non-volatile information element, such as, for example, an erasable programmable read-only memory ("EPROM"). "EPROM" as used herein includes its broad ordinary meaning known to one of skill in the art, including those devices commonly referred to as "EEPROM "EPROM," as well as any types of electronic devices capable of retaining their contents even when no power is applied and/or those types of devices that are reprogrammable. In an embodiment, the information element is an impedance value associated with the sensor, such as, for example, a resistive value, an impedance value, an inductive value, and/or a capacitive value or a combination of the foregoing. In addition, the cable's information element could be provided through an active circuit such as a transistor network, memory chip, flash device, or other identification device, including multi-contact single wire information elements or other devices, such as those commercially available from Dallas Semiconductor or the like. Moreover, the information element may be random access memory (RAM), read-only memory (ROM), or a combination of the same.

In an embodiment, the physiological monitor 810 communicates with the information element 860 via a serial transmission line 840. In one embodiment, the serial transmission line 840 is a multi-drop bus, although in alternative embodiments, the serial transmission line 840 is a 1-wire bus, a SCSI bus, or another form of bus. Once the physiological monitor 810 determines that it is connected to the sensor cable 812, it sends and receives signals to and from the information element 860 to access cable management information and/or patient context information. Alternatively, the physiological monitor 810 does not access the information element 860 until requested to do so by a user (e.g., a clinician). In addition, the physiological monitor 810 may also automatically access the information element 860 or access the information element 860 in response to a user request.

Cable management information that may be stored on the information element 860 may include information on cable usage, sensor usage, and/or monitor usage. Cable usage data may include, for example, information on the time the cable has been in use, enabling the physiological monitor 810 to determine when the sensor cable 812 is near the end of its life. Sensor usage data may include, for example, information on what sensors have been attached to the sensor cable 812, for how long, and the like. Similarly, monitor usage data may include, for example, information on what monitors have been attached to the sensor cable 812, for how long, and the like. More detailed examples of cable management information are described below, with respect to FIG. 9.

Patient context information that may be stored on the information element 860 may include patient identification data and patient flow data. In one example embodiment, patient identification data includes at least the patient's name and one or more identification numbers. Patient flow data may include, for example, details regarding the departments the patient has stayed in, the length of time therein, and devices connected to the patient. More detailed examples of patient context information may also be found below, with respect to FIG. 9.

Advantageously, in certain embodiments, the physiological monitor 810 uses the cable management information in various embodiments to determine when to replace a cable in order to prevent cable failure. The physiological monitor 810 may also use the information element 860 to track sensor 850 and physiological monitor 810 use. Some implementations of the physiological monitor 810 enable the physiological monitor 810 to transmit some or all of the cable management information to a central nurses station or to a clinician's end user device, such as is described in further detail below, with respect to FIG. 9. In some implementations, the physiological monitor 810 or a central nurses station sends an alarm to the end user device that alerts the user to impending cable failure. For example, a clinician might receive an alarm notification on a personal digital assistant (PDA), pager, or the like, which enables the clinician to replace the cable before it fails. Patient context information, including identification information, may also be provided along with the alarm to help the clinician identify the cable with the patient.

Figure 10:
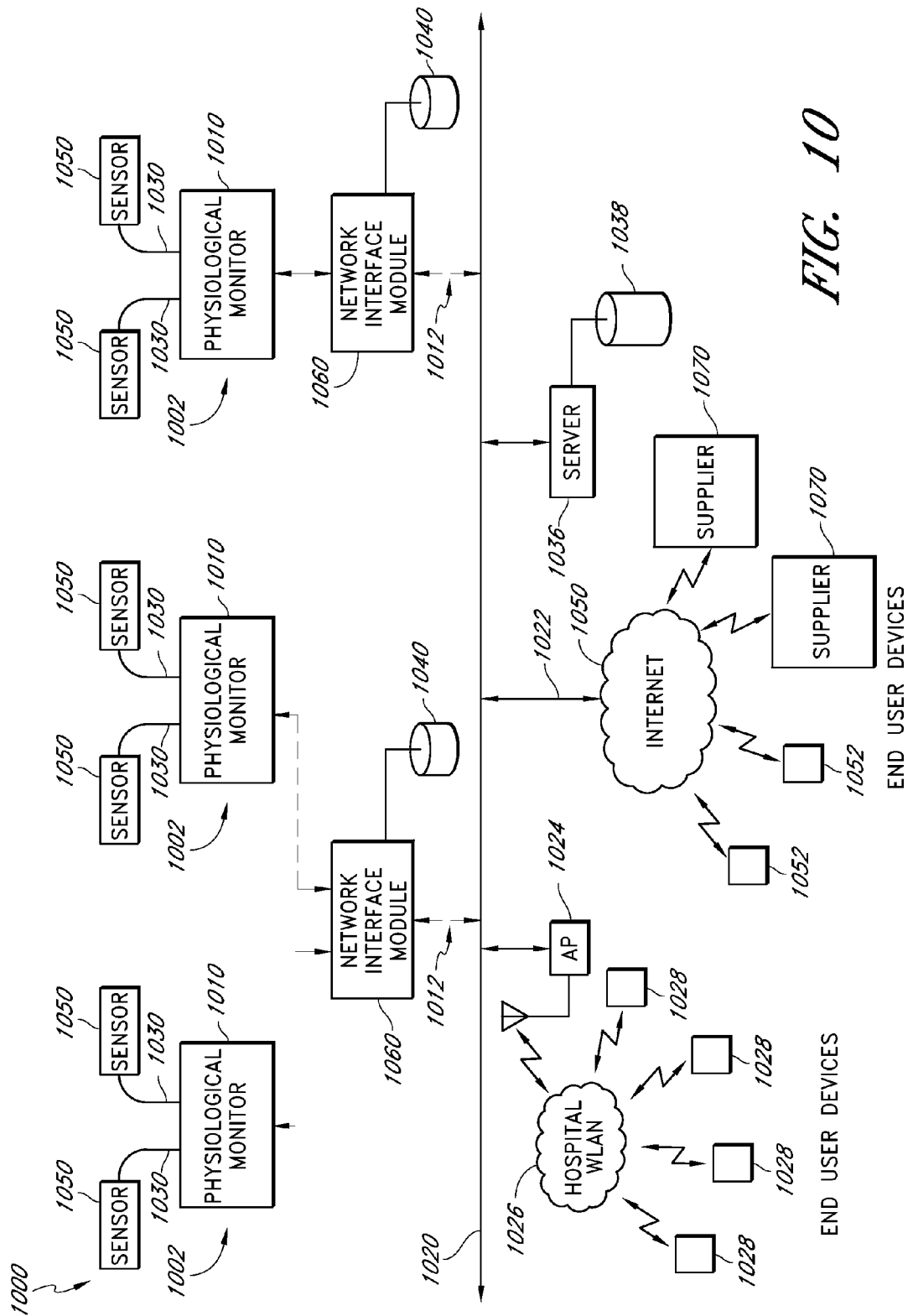
FIG. 10 illustrates an embodiment of a physiological monitoring system having multiple networked physiological monitors.

Moreover, the physiological monitor 810 may transmit some or all of the cable management information and/or patient context information to a central server (see, e.g., FIG. 10). Inventory software on the central server can use this information to preemptively order new cables when cable inventory is low or at other times.

Different sensors 850 and physiological monitors 810 may be attached to the same sensor cable 812. Thus, the cable management information may also include a list of which sensors 850 and physiological monitors 810 have been attached to the cable 812, how long they were attached, and the like. The physiological monitor 810 may also provide this information to the central server to keep track of or journal this information. The cable management information is therefore used in some embodiments to derive patient monitoring metrics, which may be analyzed to monitor or improve hospital operations. A hospital may use these metrics, for example, to determine when to replace cables or to determine whether personnel are using the cables improperly or are damaging the cables through improper use.

The patient context information in some embodiments also enables the sensor cable 812 to be identified with a particular patient. As the sensor cable 812 of some embodiments may be transported with the patient when the patient is moved about the hospital, when the sensor cable 812 is attached to different monitors 850, the data stored in the information element 860 may be transferred to the new monitor 850. Thus, during the patient's stay at the hospital or at discharge, the information element 860 of certain embodiments has patient flow data that a hospital can use to monitor or improve operations. The flow data of multiple patients may be used, for instance, to determine the number of patients staying in a particular department at a given time and the equipment used during those patients stay. Knowing this information, the hospital can adjust equipment inventories and staff assignments to more efficiently allocate hospital resources among the various departments.

FIG. 8B illustrates another embodiment of a monitoring system 800B. The monitoring system 800B preferably includes all the features of the monitoring system 800A and additionally includes an information element 862 in the instrument cable 814 and an information element 864 in the sensor 850. The information elements 862, 864 may have the same or different characteristics of the information element 860, including the same or different memory type, capacity, latency, or throughput.

In an embodiment, the serial transmission line 840 connects the physiological monitor 810 to the information element 860 in the sensor cable 812 as above. However, the serial transmission line 840 also connects to the information elements 862, 864. The physiological monitor 810 may therefore access the information elements 860, 862, 864 while running generally few transmission lines 840.

The information elements 862, 864 may have all or a portion of the functionality of the information element 860. In one embodiment, the same data is stored in each of the information elements 860, 862, 864, thereby providing data redundancy. Additionally, in such embodiments the instrument cable 814 may stay with the patient as the patient moves from one department to another, in place of or in addition to the sensor cable 812. Moreover, in one embodiment only the instrument cable 814 or the sensor assembly 850 has an information element 862 or 864, and the sensor cable 812 does not have an information element 860.

The placement of the information elements 862, 864 can be in any of a variety of locations. For example, the information element 862 may be located in either one or the connectors 831, 835 or in the instrument cable section 834. Likewise, the information element 864 of the sensor 850 may be located in the connector 851 or in another part of the sensor 850.

Although not shown, the sensor cable 812 and/or the instrument cable 814 may have multiple information elements in some embodiments. When multiple information elements are used, certain data may be stored on some information elements, and other data may be stored on others. For instance, cable management information may be stored on a separate information element from patient context information, and physiological information may be stored on yet another information element.

Figure 8C:
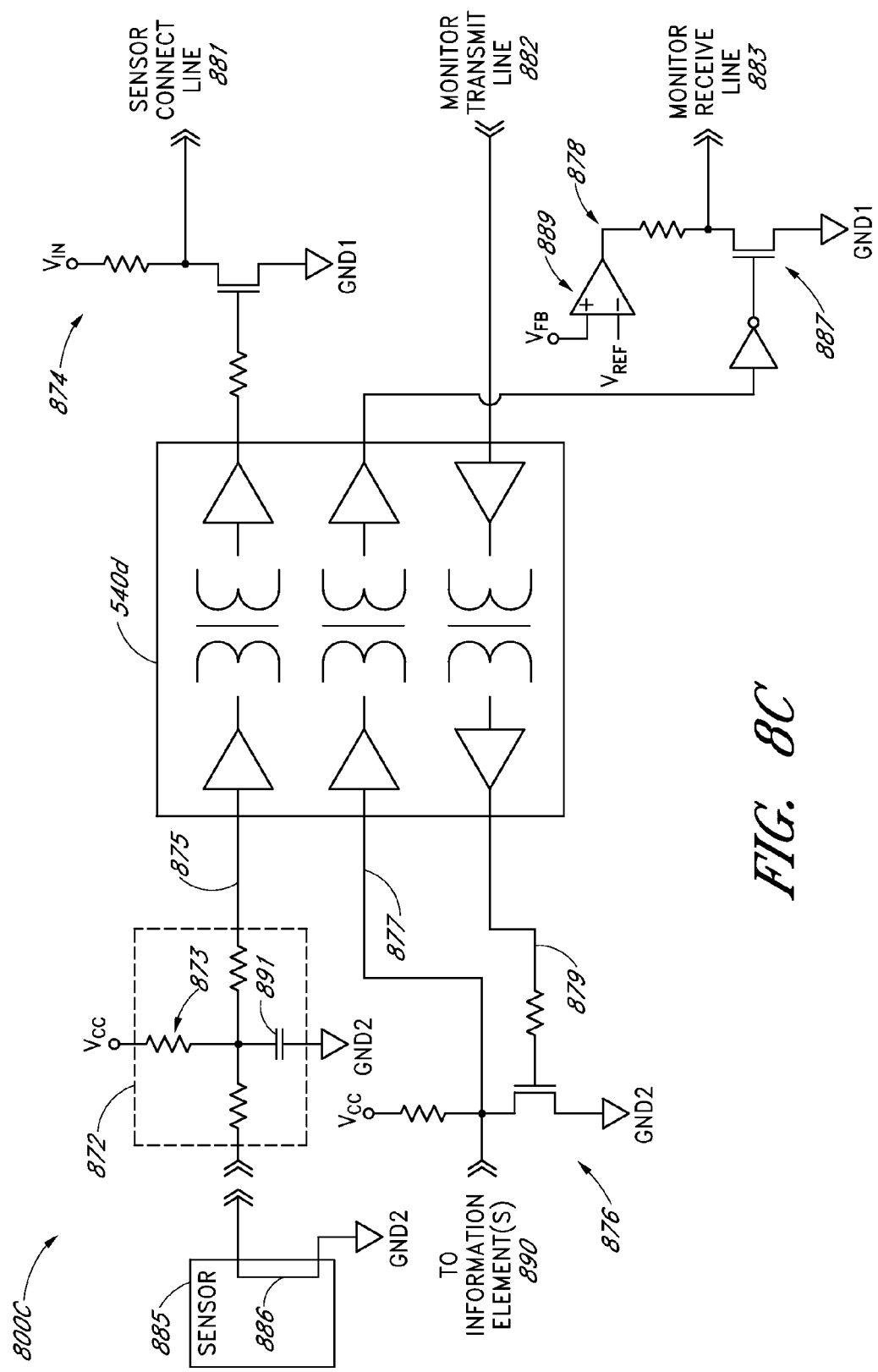
FIG. 8C illustrates an embodiment of a circuit for communicating with one or more information elements and a sensor.

FIG. 8C illustrates an embodiment of a circuit 800C for facilitating communication between a monitor and one or more information elements 890. The circuit 800C may be included in any of the cable or sensor assemblies described above, including in a splitter cable, a non-splitter cable, an instrument cable, a sensor cable, a sensor assembly, combinations of the same, and the like. In addition, the circuit 800C may be used in conjunction with the circuits 500B and 500C in a single cable, e.g., on the same circuit board, or in combination with multiple cables and/or sensor assemblies.

Advantageously, in certain embodiments, the circuit 800C provides electrical decoupling for communications lines 877, 879, 882, and 883, which provide communications between a monitor and one or more information elements. In addition, the circuit 800C may provide sensor connection status to a monitor via a sensor detect circuit 872.

A decoupling circuit 540$d$ shown includes digital decoupling logic to electrically decouple one or more information elements and one or more sensors from the monitor. The decoupling circuit 540$d$ includes transformers on a chip and associated logic that perform digital decoupling. In one embodiment, the decoupling circuit 540$d$ is a ADuM130× series chip from Analog Devices. In other embodiments, optocouplers and/or other transformers are used.

Communications lines 882, 883 allow the monitor to transmit and receive data to and from one or more information elements 890. The line 882 is a monitor transmit line 882, and the line 883 is a monitor receive line 883. Each of these lines 882, 883 is electrically decoupled from the communications line 877 by the decoupling circuit 540$d$. The communication lines 877, 879 may be electrically coupled with the one or more information elements 890.

In an embodiment, the communications line 877 is a bus, such as a 1-wire bus. The communications line 877 may be used to both transmit and receive data to and from the monitor. The communications line 879 may be used to receive data from the monitor. A MOSFET switch 876 or the like is in communication with the depicted communications line 879, which selectively transmits signals to the one or more information elements 890.

The monitor receive line 883 is in communication with a power validation circuit 878, which determines whether the feedback power VFB described above with respect to FIG. 5C is high enough. If the feedback power VFB is too low, the data received from the information elements 890 may not be used because the data may be corrupt.

In the depicted embodiment, the power validation circuit 878 includes a comparator 889 that compares the feedback power VFB with a reference voltage. If the feedback power VFB is equal to or higher than the reference voltage, the comparator 889 might output a high voltage. This high voltage can be selectively overridden by a MOSFET switch 887 in response to communications received from the information elements 890. If the feedback power VFB is lower than the reference voltage, the comparator 889 might output a low voltage. The low voltage can override the MOSFET switch 887 such that communications from the information elements 890 are not sent to the monitor.

In the depicted embodiment, sensor connection status is provided to the monitor via the sensor detect circuit 872. The sensor detect circuit 872 includes a sensor detect line 875 in communication with a pull-up resistor 873. When a sensor 885 is not connected to the line 875, the line 875 may be pulled high. This high voltage may be inverted by a MOSFET switch 874 to provide a low signal to the monitor via sensor connect line 881. The switch 874 may be omitted in some embodiments.

In response to a sensor 885 being connected to the sensor detect line 875, a shorted line 886 (or low resistance line) in the sensor 885 can cause the line 875 to be pulled low. This low value can be inverted by the switch 874 to provide a high signal to the monitor. This signal can indicate that the sensor 885 is connected. Conversely, if the sensor 885 is disconnected, the line 875 may again be pulled high, resulting in a low output of the switch 874. As a result, the monitor may receive a rapid or near-immediate indication that the sensor 885 has been disconnected.

The sensor detect circuit 872 also includes passive elements in the depicted embodiment, such as a capacitor 891, to smooth or debounce contact oscillations from the sensor 885. Thus, the sensor detect circuit 872 can also be considered a debounce circuit. In other embodiments, the sensor detect circuit 872 can be replaced with other forms of debounce circuitry.

Advantageously, in certain embodiments, the sensor detect circuit 872 can be used instead of polling the one or more information elements 890 frequently to determine if the sensor 885 is connected. Alternatively, the polling cycle of the one or more information elements 890 may be reduced. Reducing or eliminating the polling cycle can reduce power consumption by the circuit 800C.

The sensor detect circuit 872 may be used to detect the connection of cables, such as a splitter cable, as well as or instead of detecting sensor connections. In some embodiments, a sensor detect line 875 may be provided for each sensor in a multi-sensor system, each cable, or the like. Moreover, the sensor detect circuit 872 may also be used with cables that do not have a decoupling circuit.

Figure 9:
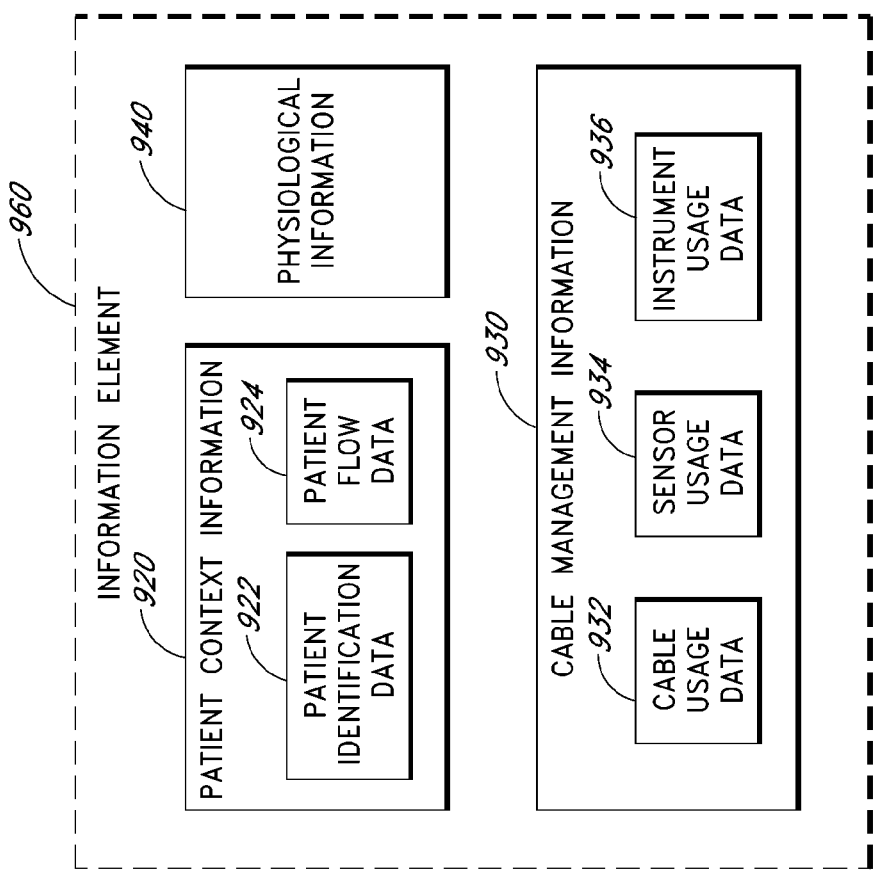
FIG. 9 illustrates a block diagram of exemplary forms of data that can be stored in an information element.

FIG. 9 illustrates a block diagram of example forms of data that can be stored on an information element. In the depicted embodiment, patient context information 920, cable management information 930, and physiological information 940 are shown. The patient context information can include patient identification data 922 and patient flow data 924. Cable management information 930 can include cable usage data 932, sensor usage data 934, and instrument usage data 936. However, while the data is depicted in FIG. 9 as comprising discrete categories, data from one category may be included within another. Data from one or more categories also may not be included, or alternatively, additional data categories than that shown may be included.

Turning to more specific examples, in one embodiment patient identification data 922 can include a patient's name, a patient's unique hospital identification number, type of patient or body tissue, information about the patient's age, sex, medications, and medical history, and other information that can be useful for the accuracy of alarm settings and sensitivities and the like. In addition, the patient identification data 922 may also include an $SpO_2$ fingerprint, determined by a pulse oximeter. In one such embodiment, the $SpO_2$ fingerprint is determined by calculating a ratio of an infrared detected wavelength and a red detected wavelength. The $SpO_2$ fingerprint can be used to detect if a sensor or cable is being improperly reused.

Patient flow data 924 can include a record of departments the patient has visited, length of stay (LOS) in those departments, overall LOS in the hospital, admittance date and time, discharge date and time, time stamps for events occurring in the hospital, and the like. Some or all of this information, in conjunction with the patient identification data, can constitute a patient flow profile.

Cable usage data may include buyer or manufacturer information cable type, serial number of the cable, date of purchase, time in use, and cable life monitoring functions (CLM), including near expiration percentage, update period, expiration limit, and an index of functions. In addition, the cable usage data 932 may include numerous read write parameters, such as the number of times the cable is connected to a monitoring system, the number of times the cable has been successfully calibrated, the total elapsed time connected to a monitor system, the number of times the cable has been connected to one or more sensors, the total time used to process patient vital parameters, the cumulative current, voltage, or power applied to the cable, the cumulative temperature of the cable, and the expiration status of the cable.

In an embodiment, the number of times the cable is placed on or removed from a patient is monitored and an indication is stored in the memory. The number of times a sensor connected to the cable is placed on or removed from a patient can be monitored by monitoring the number of probe off conditions sensed, or it can be monitored by placing a separate monitoring device on the cable or sensor to determine when a sensor clip is depressed, opened, removed, replaced, attached, or the like.

In an embodiment, the average operating temperature of the cable is monitored and an indication stored. This can be done, for example, through the use of bulk mass or through directly monitoring the temperature of the cable or the temperature of the cable's connectors. In an embodiment, the number of different monitors connected to the cable is tracked and an indication is stored in memory. In an embodiment, the number of times the cable is calibrated is monitored, and an indication is stored in memory. In an embodiment, the number of patients that use a cable is monitored and an indication is stored. This can be done by, for example, by storing sensed or manually entered information about the patient and comparing the information to new information obtained when the cable is powered up, disconnected and/or reconnected, or at other significant events or periodically to determine if the cable is connected to the same patient or a new patient. In an embodiment, a user is requested to enter information about the patient that is then stored in memory and used to determine the useful cable life. In an embodiment, a user is requested to enter information about cleaning and sterilization of the cable, and an indication is stored in the memory. Although described with respect to measuring certain parameters in certain ways, various other electrical or mechanical measurements can be used to determine any useful parameter in measuring the useful life of a cable.

Sensor usage data 934 can include some or all of the same information as the cable usage data but applied to sensors attached to the cable, and may also include information on the type or operation of the sensor, type or identification of a sensor buyer, sensor manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the sensor usage data 934 can also include emitter wavelength correction data.

Sensor usage data 934 can also include the number of emitting devices, the number of emission wavelengths, data relating to emission centroids data relating to a change in emission characteristics based on varying temperature, history of the sensor temperature, current, or voltage, emitter specifications, emitter drive requirements, demodulation data, calculation mode data, the parameters it is intended to measure (e.g., HbCO, HbMet, etc.) calibration data, software such as scripts, executable code, or the like, sensor electronic elements, whether it is a disposable, reusable, or multi-site partially reusable, partially disposable sensor, whether it is an adhesive or non-adhesive sensor, whether it is reflectance or transmittance sensor, whether it is a finger, hand, foot, forehead, or ear sensor, whether it is a stereo sensor or a two-headed sensor, sensor life data indicating whether some or all sensor components have expired and should be replaced, encryption information, keys, indexes to keys or has functions, or the like monitor or algorithm upgrade instructions or data, and some or all of parameter equations.

Instrument usage data 936 can include buyer or manufacturer information, information on the type of monitors that the cable has connected to, number of monitors the cable has connected to, duration of cable connections to the monitors, duration of use of the monitor, trend history, alarm history, sensor life, an identification number for a specific monitor, and the like. In addition, the instrument usage data 936 may include all or a portion of all the cable and sensor usage data described above.

The physiological information 940 may include any of the physiological parameters described above, obtained from the sensors or monitors attached to the information element 960. In one implementation, the information element 960 enables the physiological information 940 to be transferred between physiological monitors. As a result, a historical view of the patient's physiological parameters may be provided to different monitors throughout the hospital. Thus, clinicians in different departments can observe the patient's physiological information obtained in a previous department, enabling clinicians to provide a higher quality of care.

FIG. 10 illustrates an embodiment of a physiological monitoring system 1000 which may be used in a hospital, nursing home, or other location where medical services are administered (collectively "hospital"). Certain aspects of the physiological monitoring system 1000 are described in more detail in U.S. patent application Ser. No. 11/633,656, titled "Physiological Alarm Notification System," filed Dec. 4, 2006, which is hereby incorporated by reference in its entirety.

The physiological monitoring system 1000 of certain embodiments includes patient monitoring devices 1002. The patient monitoring devices 1002 of various embodiments include sensors 1050, one or more physiological monitors 1010, cables 1030 attaching the sensors 1050 to the monitors 1010, and a network interface module 1006 connected to one or more physiological monitors 1010. Each patient monitoring device 1002 in some embodiments is part of a network 1020 of patient monitoring devices 1002. As such, the patient monitoring devices 1002 in these embodiments can communicate physiological information and alarms over a hospital wireless network (WLAN) 1026 or the Internet 1050 to clinicians carrying end user devices 1028, 1052.

The network interface module 1002 of certain embodiments transmits physiological information on demand or in the event of an alarm to the end-user devices 1028, 1052 and/or transmits the alarm to a central nurses station. Alternatively, the network interface module 1002 transmits information and alarms to a server 1036. The server 1036 is a computing device, such as an appliance server housed in a data closet or a workstation located at a central nurses station. The server 1036 passes the information or alarms to the end user devices 1028, 1052 or to the central nurse's station. The alarms may be triggered when certain physiological parameters exceed safe thresholds, thereby enabling clinicians to respond rapidly to possible life-threatening situations. Situations giving rise to an alarm might include, for example, decreased heart rate, respiratory rate, low $SpO_2$ levels, or any other physiological parameter in an abnormal range.

The network interface module 1002 in one embodiment also performs cable management by generating an alarm when one of the cables 1030 is nearing the end of its life. The network interface module 1002 determines whether the cable's 1030 life is close to expiring by, for example, analyzing some or all of the data described above with respect to FIG. 9. In one embodiment, if the network interface module 1002 determines that the cable life is close to expiration, the network interface module 1002 provides an expiration message as an alarm.

In one embodiment, the server 1036 receives this expiration message. The server 1036 then checks an inventory stored in a database 1038 to see if a replacement cable is available. If there is no replacement cable in the inventory, the server may forward the message to a supplier 1070 over the Internet 1050 (or through a WAN, leased line or the like). In an embodiment, the server 1036 transmits an email message to a supplier 1070 that indicates the cable location, cable condition, and/or other cable usage data. The supplier 1070 in one embodiment is a cable seller. Upon receiving the message, the supplier 1070 may automatically ship a new cable to the hospital. Consequently, cable 1030 inventories are able to be maintained with minimal or no user intervention in this implementation, and cables 1030 may be replaced preemptively, before cable failure.

In additional embodiments, the network interface module 1006 may monitor sensor utilization, such as the number of sensors used during the patient's stay, the types of sensors, and the length of time in use before replacement. Such data can be used by the hospital to preemptively plan restocking and set department par inventory levels. In addition, a supplier can use this data to restock the hospital or implement a just in time inventory control program. Moreover, such information can be used by the supplier to improve overall cable reliability and for the hospital to better plan and manage consumables.

The network interface module 1006 of various implementations also performs context management. In one embodiment, context management includes associating context information with physiological information to form a contextual data package. As described above, context information may include patient identification data and patient flow data. In addition, context information may include context information related to usage of the network interface module 1006 and context information related to the network. For example, this additional context information may include an identification number of the network interface module 1006, time stamps for events occurring in the physiological monitoring system 1000, environmental conditions such as changes to the state of the network and usage statistics of the network interface module 1006, and identification information corresponding to the network (e.g., whether the network connection is WiFi or Ethernet).

The network interface module 1006 receives context information in one embodiment by a nurse entering the information in the network interface module 1006 or from the server 1036. The network interface module 1006 transmits or communicates the contextual data package to clinicians during an alarm, upon clinician request, or on a scheduled basis. In addition, the network interface module 1006 may transmit a continuous stream of context information to clinicians.

The server 1036 receives contextual data packages from a plurality of network interface modules 1006 and stores the contextual data package in a storage device 1038. In certain embodiments, this storage device 1038 therefore archives long-term patient data. This patient data may be maintained even after the patient is discharged. Thus, context information may be stored for later analysis to, for example, develop patient care metrics and improve hospital operations. The patient data could be deleted after the care metrics are developed to protect patient privacy.

Although the functions of cable management and context management have been described as being performed by the network interface module 1006, in certain embodiments, some or all of these functions are instead performed by the physiological monitor 1010. In addition, the physiological monitor 1010 and the network interface module 1006 may both perform cable management and/or context management functions.

Figure 11:
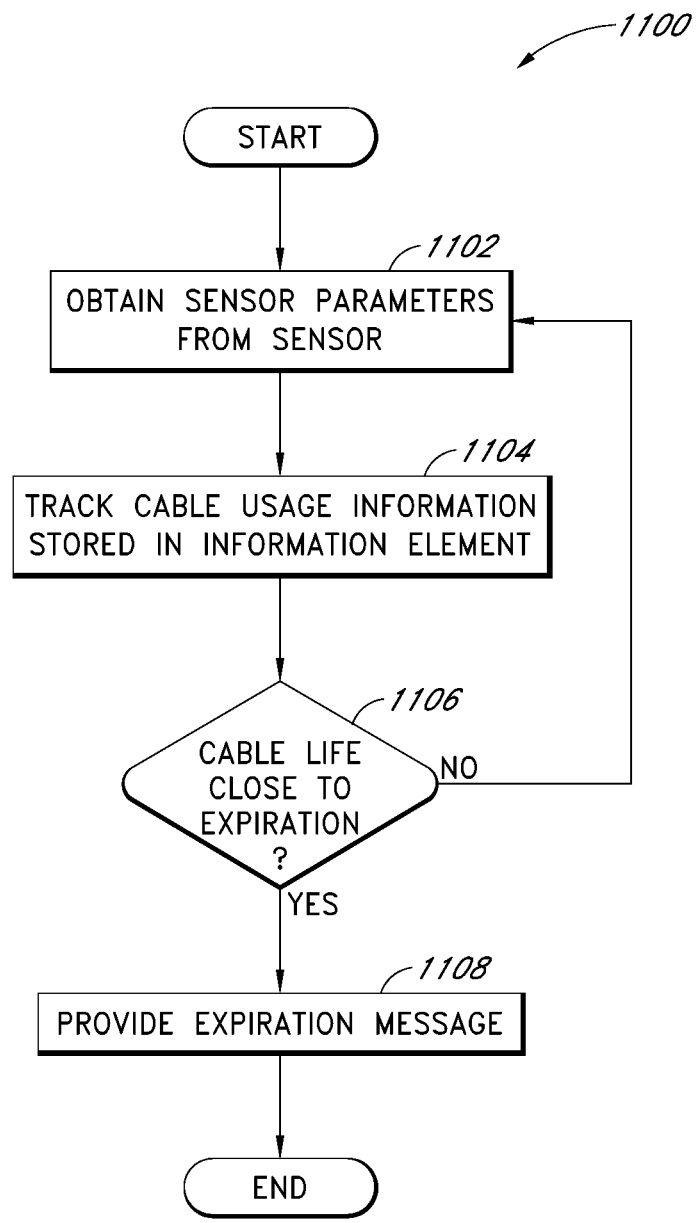
FIGS. 11 and 12 illustrate flowchart diagrams of example cable management processes.

FIG. 11 illustrates an embodiment of a usage tracking method 1100 for tracking the life of a medical cable. In one implementation, the usage tracking method 1100 is performed by the network interface module and/or one of the physiological monitors described above. More generally, the usage tracking method 1100 may be implemented by a machine having one or more processors. Advantageously, in certain embodiments, the usage tracking method 1100 facilitates replacing a cable prior to failure of that cable.

The usage tracking method 1100 begins by obtaining sensor parameters from a sensor at block 1102. At block 1104, cable usage information stored in an information element is tracked. The cable usage information can be tracked by at the same time or substantially the same time as obtaining sensor parameters from the sensor. Alternatively, the cable usage information may be tracked by determining cable usage at the start or end of monitoring (e.g., obtaining sensor parameters), or periodically throughout monitoring. In addition, the cable usage information may be tracked even if the block 1102 were not performed, e.g., when the monitor is not currently obtaining parameters from the sensor.

At decision block 1106, it is determined whether the cable's life is close to expiring (or whether the cable has in fact expired). This determination may be made using the data described above with respect to FIG. 9. In addition, the this determination may be made using sensor life functions applied analogously to the life of the cable.

If it is determined that the cable life is close to expiration (or has expired), an expiration message is provided at block 1108. In one embodiment, this message is provided as an alarm on the monitor or at a central nurses station. The message may also be provided to a clinician's end user device, which may be located in the hospital or at a remote location. Moreover, the message may be provided to a server, which forwards the message to a supplier, which ships a new cable. In an embodiment, the message is an email that indicates the cable location, cable condition, and/or other cable usage data. If, however, it is determined that the cable life is not close to expiration (or is not expired), the usage tracking method 1100 loops back to block 1102 to continue monitoring. In effect, the usage tracking method 1100 may continue monitoring and/or tracking cable usage information until the cable is close to expiration or has expired.

Figure 12:
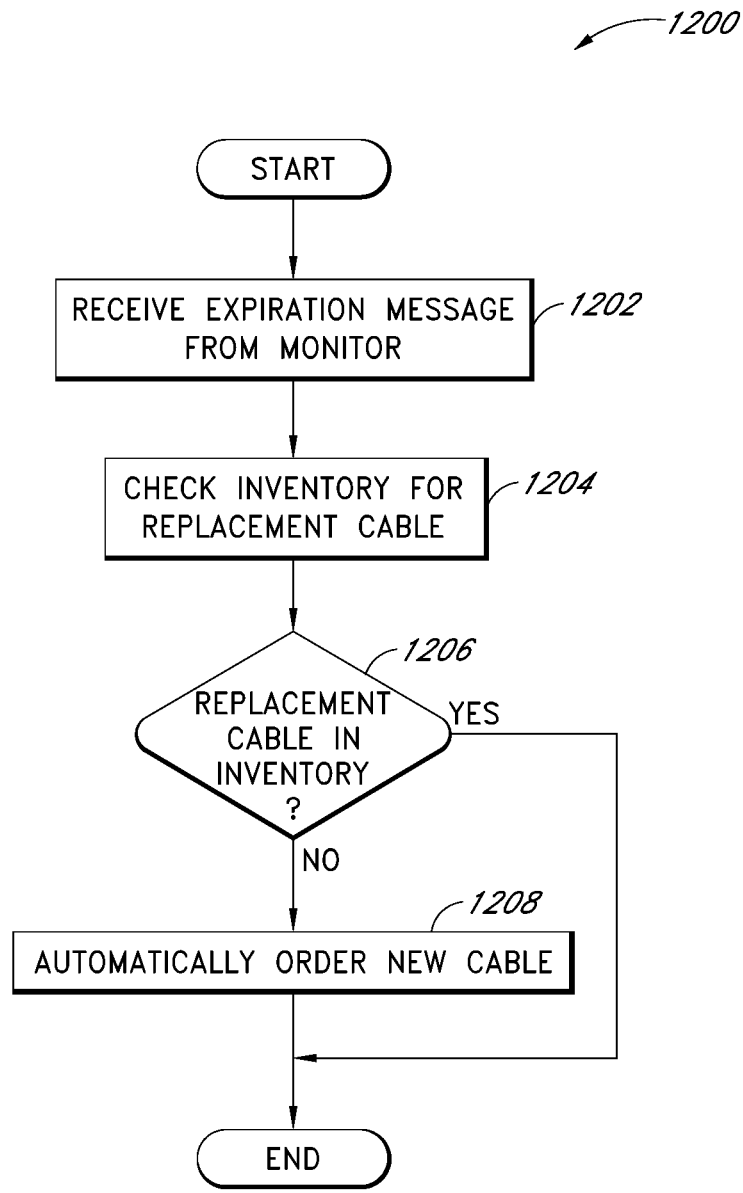

FIG. 12 illustrates an embodiment of a cable inventory method 1200 for controlling cable inventory. The cable inventory method 1200 may be performed by a server, such as the server 1038 described above. More generally, the cable inventory method 1200 may be implemented by a machine having one or more processors. In one embodiment, the method 1200 is performed in response to the method 1100 providing an expiration message at step 1108.

At block 1202, an expiration message is received from a monitor, indicating that a cable is close to expiration or has expired. At block 1204, an inventory is checked for a replacement cable. This inventory may be a hospital inventory, a record of which may be maintained in a hospital database or the like.

If it is determined at decision block 1206 that there is no replacement cable in the inventory, a new cable is ordered automatically to order a at block 1208. In an embodiment, this block 1208 is performed by electronically contacting a supplier to order the cable, for example, by sending a request over a network such as the Internet. Consequently, in certain embodiments, the cable inventory method 1200 enables the cable to be replaced preemptively, before cable failure. If, however, there is a replacement cable in inventory, the cable inventory method 1200 ends. However, in alternative embodiments, the cable inventory method 1200 orders a replacement cable regardless of the inventory, such that a predetermined level of cable inventory is maintained.

In additional embodiments, the cable inventory method 1200 may monitor sensor utilization, such as the number of sensors used during the patient's stay, the types of sensors, and the length of time in use before replacement. Such data can be used by the hospital to preemptively plan restocking and set department par inventory levels. In addition, a supplier can use this data to restock the hospital or implement a just-in-time program. Moreover, such information can be used by the supplier to improve overall cable reliability, and for the hospital to better plan and manage consumables.

Figure 13:
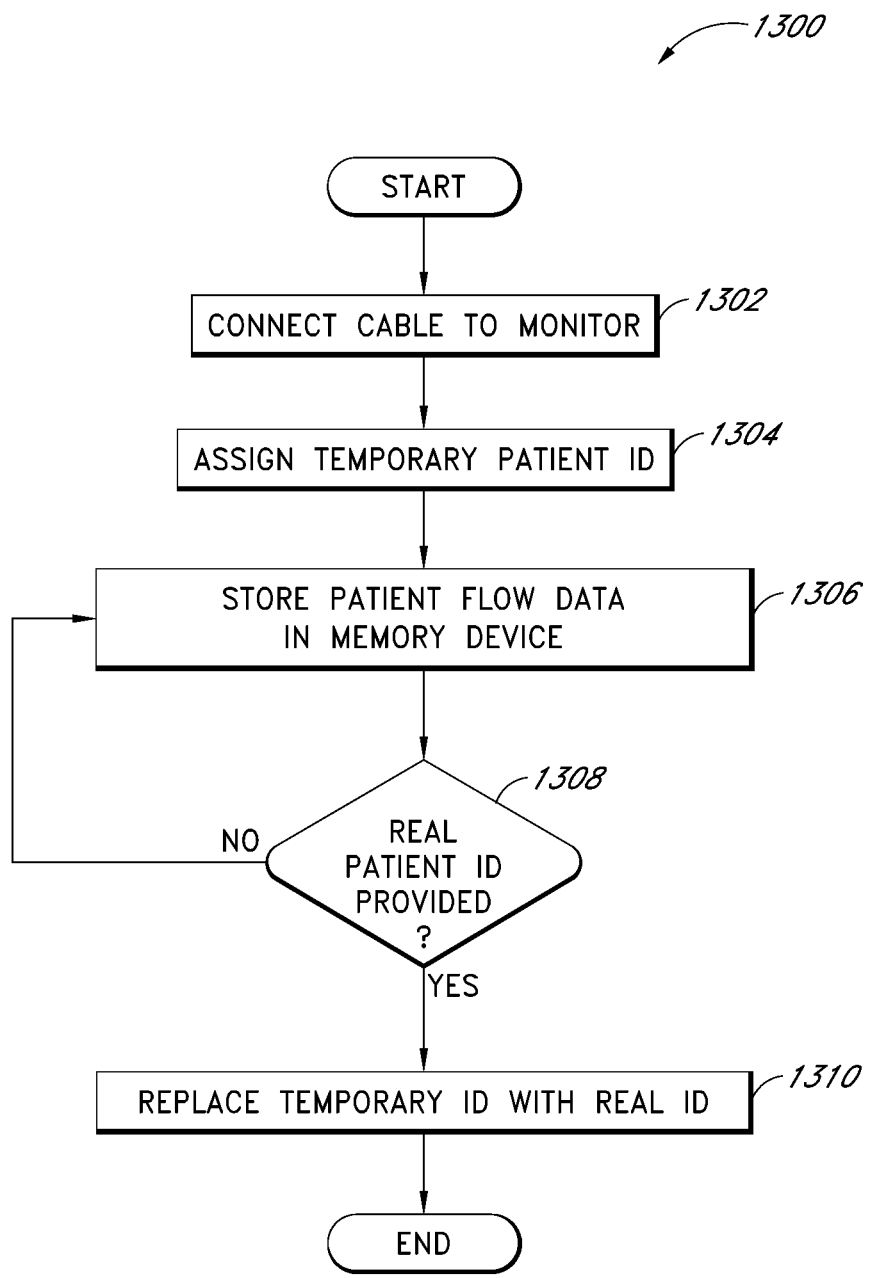
FIGS. 13 and 14 illustrate flowchart diagrams of example patient context management processes.

FIG. 13 illustrates an example context management method 1300 for managing patient context. In an embodiment, the context management method 1300 is performed by a physiological monitor, such as any of the monitors described above. More generally, certain blocks of the context management method 1300 may be implemented by a machine having one or more processors. The context management method 1300, in certain embodiments, advantageously enables a patient to be assigned a cable with a unique identifier upon the first connection of the cable to the patient or to a monitor.

At block 1300, a cable is connected to a monitor, for example, by a clinician such as a nurse. Thereafter, a temporary patient ID is assigned to the cable at block 1304. The temporary ID may be automatically assigned when power is provided to the information element in the cable, or a prompt may be provided to a clinician, who then assigns the ID. In addition, the temporary ID may also be previous stored on the cable. The temporary patient ID enables the cable to be identified as uniquely relating to the patient, prior to the patient's identification information being provided to the cable. The temporary patient ID may be stored in the information element of the cable.

At block 1306, patient flow data is stored in the information element. The patient flow data may include flow data described above with respect to FIG. 9. For example, the patient flow data may include information regarding connected devices, a department ID associated with the cable, and time spent by the cable in a department. By storing patient flow data, the context management method 1300 can enable the flow of the patient may be monitored upon connection of the cable to a monitor. Thus, even if the nurse neglects to identify the cable with the patient, the cable can have data indicating when it is being used on the same or a different patient.

At decision block 1308 it is determined whether a real patient ID has been provided. If so, then the temporary ID is replaced with the real patient ID at block 1310. The real patient ID may include any of the patient identification information described above, with respect to FIG. 13. If, however, it is determined that a real patient ID has not been provided, the context management method 1300 loops back to block 1306 to continue storing patient flow data in the information element.

Figure 14:
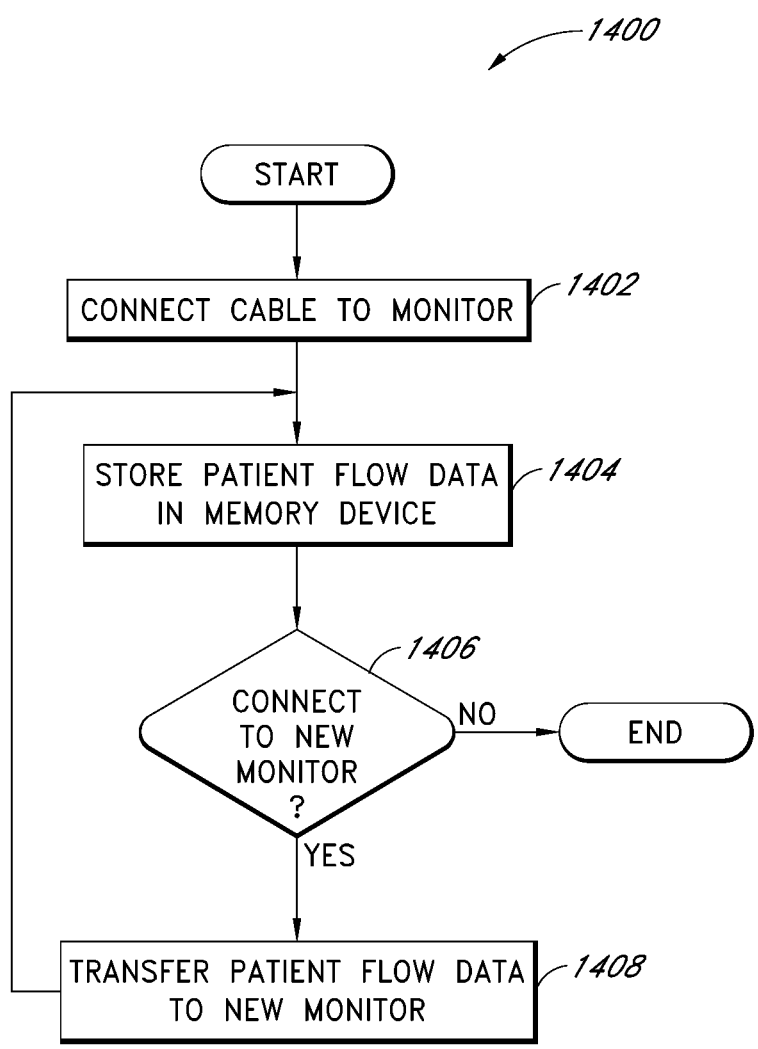

FIG. 14 illustrates another example context management method 1400 for managing patient context. In an embodiment, the context management method 1400 is performed by one or more monitors, such as any of the monitors described above. More generally, certain blocks of the context management method 1400 may be implemented by a machine having one or more processors.

At block 1402, a cable is connected to a monitor. In one embodiment, this block is performed by a clinician, such as a nurse. Patient flow data is then stored in an information element at block 1404. The patient flow data may include the flow data described above with respect to FIG. 9.

At decision block 1406, it is determined whether the cable has been connected to a new monitor. If it has, patient flow data is transferred from the cable to the new monitor at block 1408. In an embodiment, the new monitor determines whether the cable has been connected to the new monitor. Alternatively, the cable makes this determination. Transferring the patient flow data to the new monitor provides, in certain embodiments, the advantage of enabling the monitor to know where the patient has been in the hospital and for how long. If a new monitor has not been connected, the context management method 1400 ends.

Those of skill in the art will understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

Those of skill will further appreciate that the various illustrative logical blocks, modules, circuits, and algorithm steps described in connection with the embodiments disclosed herein may be implemented as electronic hardware computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of this disclosure.

The various illustrative logical blocks, modules, and circuits described in connection with the embodiments disclosed herein can be implemented or performed with a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A computer-readable storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, and/or variables.

In addition, although certain inventions have been disclosed in the context of certain embodiments, it will be understood by those skilled in the art that the inventions disclosed herein extend beyond the specifically disclosed embodiments to other alternative embodiments and/or uses of the inventions and obvious modifications and equivalents thereof. In particular, while the system and methods have been described in the context of certain embodiments, the skilled artisan will appreciate, in view of the present disclosure, that certain advantages, features and aspects of the acoustic signal processing system, device, and method may be realized in a variety of other applications and software systems. Additionally, it is contemplated that various aspects and features of the inventions disclosed herein can be practiced separately, combined together, or substituted for one another, and that a variety of combination and subcombinations of the features and aspects can be made and still fall within the scope of the inventions disclosed herein. Furthermore, the systems described above need not include all of the modules and functions described in certain embodiments. Thus, it is intended that the scope of the inventions disclosed herein disclosed should not be limited by the particular disclosed embodiments described above, but should be determined only by the claims that follow.

What is claimed is:

1. A pulse oximetry system for reducing the risk of electric shock to a medical patient, the pulse oximetry system comprising:

a plurality of physiological sensors, at least one of the physiological sensors comprising:
  a light emitter configured to impinge light on body tissue of a living patient, the body tissue including pulsating blood, and
  a detector responsive to the light after attenuation by the body tissue, wherein the detector is configured to generate a signal indicative of a physiological characteristic of the living patient; and
a physiological monitor, the physiological monitor configured to receive the signal from the at least one physiological sensor and determine the physiological characteristic of the living patient; and
a splitter cable comprising:
  a monitor connector operative to connect to a physiological monitor,
  a plurality of sensor connectors each operative to connect to one of the physiological sensors,
  a plurality of cable sections each disposed between a sensor connector and the monitor connector, each of the cable sections comprising one or more electrical conductors, the one or more electrical conductors for at least some of the cable sections comprising:
    a power line configured to supply power to one or more of the plurality of physiological sensors;
    a signal line configured to transmit the physiological signals from one or more of the physiological sensors to the physiological monitor; and
    a ground line configured to provide an electrical return path for the power line;
  one or more decoupling circuits in communication with at least one power line, signal line, and ground line, the one or more decoupling circuits configured to communicate physiological signals between one or more of the physiological sensors and the physiological monitor, the one or more decoupling circuits operative to electrically decouple the physiological sensors from each other, wherein the one or more decoupling circuits are configured to substantially prevent ground loops from forming in the ground line;
  an information element configured to store cable management information, patient context information, or physiological information; and
  a digital decoupling circuit comprising digital decoupling logic configured to electrically decouple the information element from the monitor; and
  wherein at least one physiological sensor comprises a second information element configured to store additional cable management information, additional patient context information, or additional physiological information, wherein the digital decoupling circuit is further configured to electrically decouple the information element from the second information element.

2. The pulse oximetry system of claim 1, wherein the one or more decoupling circuits comprise an optocoupler in communication with the signal line.

3. The pulse oximetry system of claim 1, wherein the one or more decoupling circuits comprise a flyback transformer in communication with the power line.

4. The pulse oximetry system of claim 1, wherein the plurality of physiological sensors comprise an acoustic sensor.

5. A medical apparatus adapted to reduce the risk of electric shock to a medical patient when used with a physiological monitor, the apparatus comprising:

a plurality of physiological sensors, at least one of the physiological sensors comprising:
  a light emitter configured to impinge light on body tissue of a living patient, the body tissue including pulsating blood, and
  a detector responsive to the light after attenuation by the body tissue, wherein the detector is configured to generate a signal indicative of a physiological characteristic of the living patient;
a splitter cable operative to connect the plurality of physiological sensors to a physiological monitor, the splitter cable comprising a plurality of cable sections each comprising one or more electrical conductors configured to interface with one of the physiological sensors;
one or more decoupling circuits disposed in the splitter cable, the one or more decoupling circuits being in communication with at least one electrical conductor, the one or more decoupling circuits configured to communicate physiological signals between one or more of the physiological sensors and the physiological monitor, the one or more decoupling circuits operative to electrically decouple the physiological sensors from each other;
at least one information element configured to store cable management information, patient context information, or physiological information; and
a digital decoupling circuit comprising digital decoupling logic; and
wherein at least one physiological sensor comprises a second information element configured to store additional cable management information, additional patient context information, or additional physiological information, wherein the digital decoupling circuit is configured to electrically decouple the information element from the second information element.

6. The apparatus of claim 5, wherein the one or more decoupling circuits comprise one or more of an optocoupler, a transformer, and an optical fiber.

7. The apparatus of claim 5, wherein the one or more decoupling circuits comprise one decoupling circuit disposed in a monitor connector of the splitter cable.

8. The apparatus of claim 5, wherein the one or more decoupling circuits comprise a plurality of decoupling circuits disposed in sensor connectors of the splitter cable.

9. The apparatus of claim 5, wherein the plurality of decoupling circuits are disposed in all but one of the cable sections.

10. The apparatus of claim 5, wherein the plurality of physiological sensors comprise an optical sensor and an acoustic sensor.

11. The apparatus of claim 5, further comprising a sensor detect circuit configured to provide an indication of a connection status of one of the sensors without polling the sensor.

12. The apparatus of claim 5, wherein one or more of the cable sections comprise a power line configured to supply power to one of the physiological sensors, a signal line configured to transmit the physiological signals from the physiological sensor to the physiological monitor, and a ground line configured to provide an electrical return path for the power line.

13. The apparatus of claim 12, wherein the one or more decoupling circuits are configured to substantially prevent ground loops from forming in the ground line.

14. A method of reducing the risk of electric shock to a medical patient as used with a pulse oximeter, the method comprising:
  providing a plurality of physiological sensors, at least one of the physiological sensors comprising a light emitter configured to impinge light on body tissue of a medical patient and a detector configured to generate a signal indicative of a physiological characteristic of the living patient responsive to the light after attenuation by the body tissue;

providing a medical cable assembly comprising:
an information element configured to store cable management information, patient context information, or physiological information; and
a digital decoupling circuit comprising digital decoupling logic; and
one or more electrical conductors configured to allow communication between the plurality of physiological sensors and a physiological monitor, such that the medical cable assembly is operative to provide signals representing physiological information of a medical patient from the plurality of physiological sensors to the physiological monitor;

electrically decoupling the plurality of physiological sensors from each other using one or more decoupling circuits disposed in the medical cable assembly, the one or more decoupling circuits being in communication with the plurality of physiological sensors and with the physiological monitor;

electrically decoupling the information element from the physiological monitor with the digital decoupling circuit;

wherein at least one physiological sensor comprises a second information element configured to store additional cable management information, additional patient context information, or additional physiological information; and electrically decoupling the information element from the second information element with the digital decoupling circuit.

15. The method of claim 14, wherein electrically decoupling the plurality of physiological sensors from each other comprises electrically decoupling the plurality of physiological sensor from each other using an optocoupler.

16. The method of claim 14, wherein electrically decoupling the plurality of physiological sensors from each other comprises electrically decoupling the plurality of physiological sensor from each other using a transformer.

17. The method of claim 14, further comprising providing an indication of a connection status of one of the sensors without polling the sensor.

18. The method of claim 14, wherein providing the medical cable assembly further comprises providing at least one sensor cable configured to be coupled with at least one of the physiological sensors and at least one instrument cable configured to be coupled with the at least one sensor cable and with the physiological monitor.

19. The method of claim 14, wherein providing the medical cable assembly comprises providing a splitter cable.

* * * * *